(12) United States Patent
Schweitzer

(10) Patent No.: US 11,672,689 B2
(45) Date of Patent: Jun. 13, 2023

(54) ANCHOR AND BRACE FOR CORRECTING INGROWN NAILS

(71) Applicant: Jordan Schweitzer, Edmonds, WA (US)

(72) Inventor: Jordan Schweitzer, Edmonds, WA (US)

(*) Notice: Subject to any disclaimer, the term of this patent is extended or adjusted under 35 U.S.C. 154(b) by 289 days.

(21) Appl. No.: 16/681,585

(22) Filed: Nov. 12, 2019

(65) Prior Publication Data

US 2020/0146868 A1 May 14, 2020

Related U.S. Application Data

(60) Provisional application No. 62/760,042, filed on Nov. 13, 2018.

(51) Int. Cl.
*A61F 5/11* (2006.01)
(52) U.S. Cl.
CPC ..................... *A61F 5/11* (2013.01)
(58) Field of Classification Search
CPC .......... A61F 5/10; A61F 5/11; A61F 5/05866; A61F 5/00; A61F 5/04; A61F 5/05; A61F 5/058; A61F 5/05841; A61F 5/05875; A45D 29/00; A45D 29/06; A45D 29/22; A61B 17/0466; A61B 17/08; A61B 17/083; A61B 17/085; A61B 17/04
USPC .......................................................... 602/31
See application file for complete search history.

(56) References Cited

U.S. PATENT DOCUMENTS

| | | | | |
|---|---|---|---|---|
| 884,376 | A * | 4/1908 | Foster | A61F 5/11 602/31 |
| 1,708,716 | A * | 4/1929 | Andersen | A61F 5/11 602/31 |
| 2,499,851 | A | 3/1950 | Cronholm | |
| 4,057,055 | A * | 11/1977 | Clark | A61F 5/11 602/31 |
| 5,261,872 | A | 11/1993 | Goldenberg | |
| 2010/0137771 | A1 | 6/2010 | Harada | |
| 2011/0022082 | A1* | 1/2011 | Burke | A61B 17/083 606/214 |
| 2013/0153628 | A1* | 6/2013 | Euteneuer | A61B 17/0642 227/175.1 |
| 2016/0310140 | A1* | 10/2016 | Belson | A61B 17/08 |

* cited by examiner

*Primary Examiner* — Rachael E Bredefeld
*Assistant Examiner* — Trisha Talapatra
(74) *Attorney, Agent, or Firm* — Seed IP Law Group LLP

(57) ABSTRACT

System, devices, and methods for correcting ingrown nails are disclosed. A system includes a first anchor and a second anchor configured to be coupled to opposing sides of an ingrown nail of an end user. A first brace and a second brace are configured to be removably coupled to respective ones of the first and second anchors. An elastic loop is secured between the protrusions of the braces to apply continuous tension to the braces. The tension is distributed to the nail through the anchors to which the braces are coupled. The amount of tension applied to the nail can be selected by selecting different elastic loops to attach to the braces. The tension provided by the elastic loops corrects the ingrown nail over time without pain to the user.

20 Claims, 12 Drawing Sheets

ANCHOR AND BRACE FOR CORRECTING INGROWN NAILS

BACKGROUND

Technical Field

The present disclosure is directed to devices, systems and methods for correcting ingrown nails, and more particularly, to anchors and braces for providing continuous tension on ingrown nails.

Description of the Related Art

An ingrown nail (onychocryptosis) is a common medical problem that occurs when a nail, such as a toe nail, for example, folds inwards towards the skin beneath the nail comprising the nail bed and grows into the nail bed instead of over it. In other words, ingrown nails are an abnormal embedding of the nail plate into the nail groove. The result of an ingrown nail can be pain, redness, swelling, and in some cases, an infection. These symptoms can also result in broader negative consequences, such as insomnia, loss of mobility, or continuous pain and discomfort, among others.

A consultation with a licensed medical professional, such as a primary care provider, a podiatrist, or a dermatologist, is a popular treatment option for correcting an ingrown nail. However, as with other forms of medical treatment, such consultations, which may include surgery to correct the ingrown nail, interrupt normal daily activities and are prohibitively expensive for many users.

In response, home treatment devices and methods have been proposed as an alternative to professional assistance. However, current home treatment devices and methods for correcting ingrown nails suffer from a number of deficiencies. First, many known ingrown nail treatment devices and methods are not effective for severely ingrown toe nails. Second, known devices and methods can cause significant pain to the user. Third, some known devices and methods utilize a device that is attached to the nail for the duration of treatment that is too large to wear with most footwear, which renders these solutions impractical for the day to day activities of the user. Finally, known treatment devices and methods may require significant amounts of time, such as up to a month or more, to correct the ingrown nail. As such, known devices and methods for correcting ingrown nails do not provide an effective solution, which leaves consumers with an option between expensive professional treatments or ineffective home remedies that can cause prolonged pain and discomfort while ineffectively attempting to treat the problem.

BRIEF SUMMARY

The present disclosure is directed to a nail corrector for straightening nails that are digging into skin or have an unattractive curve. Disclosed is a way to address the issue of ingrown nails that reduces pain for end users while providing an alternative to surgery or painful home remedies which are often ineffective.

Disclosed is a non-invasive way to help straighten a nail by applying continuous tension. Anchors are coupled to the toe nail and a brace is coupled to each anchor. A resilient connection member, such as a rubber band, is attached extending from one brace to the other to pull the nail towards a flattened shape. The amount of tension delivered is selected based on the strength of the resilient connection member, for example, by selecting between different rubber bands which allow for varying tension levels. The design of the anchors allows for the rubber bands to be securely held in place with tension or pressure distributed back onto the nail to straighten the nail.

Specifically, the present disclosure describes systems, devices, and methods for correcting ingrown nails by utilizing sets of anchor and brace pairs to apply continuous tension to the nail. Each of the anchors is attached, with an adhesive, to opposite sides of an ingrown nail. Each of the anchors includes at least one aperture through the anchor and each of the braces has at least one first protrusion and a second protrusion. The first protrusion of each brace is removably positioned in the at least one aperture of a respective anchor to couple the brace to the anchor. Then, a resilient connection member, such as an elastic loop or a rubber band, is coupled to each of the second protrusions of the opposing braces. The resilient connection member applies continuous tension to the braces, which is distributed to the nail through the anchors. The amount of tension applied to the nail can be varied by using different sizes or types of resilient connection members with different elastic properties.

The continuous application of tension to the nail corrects the ingrown nail over a shorter period of time than with other known devices and methods. In addition, the continuous application of tension and the design of the anchors do not result in pain for the end user, but rather, reduce or prevent pain from the ingrown nail because the nail is pulled away from the nail bed by the tension. Because the braces and anchors are relatively small in size, the braces and anchors can often be worn by the user with their current shoes or other footwear. Thus, the toe nail is corrected over a few days of time, without significantly impacting the day to day activities of the user. Moreover, the braces can be removed, if desired, to further reduce the height of the correcting device to further reduce the impact on the day to day activities of the user.

The present disclosure also describes additional systems, methods, and devices for correcting ingrown nails including two single piece devices, wherein each device is coupled to the ingrown nail and a resilient connection member is coupled between the devices to create tension, as above. In other words, in one or more embodiments, the anchors and braces are combined into a single device as opposed to being two separate devices. Further embodiments include methods of manufacturing and operation of the same.

BRIEF DESCRIPTION OF THE SEVERAL VIEWS OF THE DRAWINGS

For a better understanding of the embodiments, reference will now be made by way of example only to the accompanying drawings. In the drawings, identical reference numbers identify similar elements or acts. In some figures, the structures are drawn to scale. In other figures, the sizes and relative positions of elements in the drawings are not necessarily drawn to scale. For example, the sizes, shapes of various elements and angles may be enlarged and positioned in the figures to improve drawing legibility.

DETAILED DESCRIPTION

Figure 1:
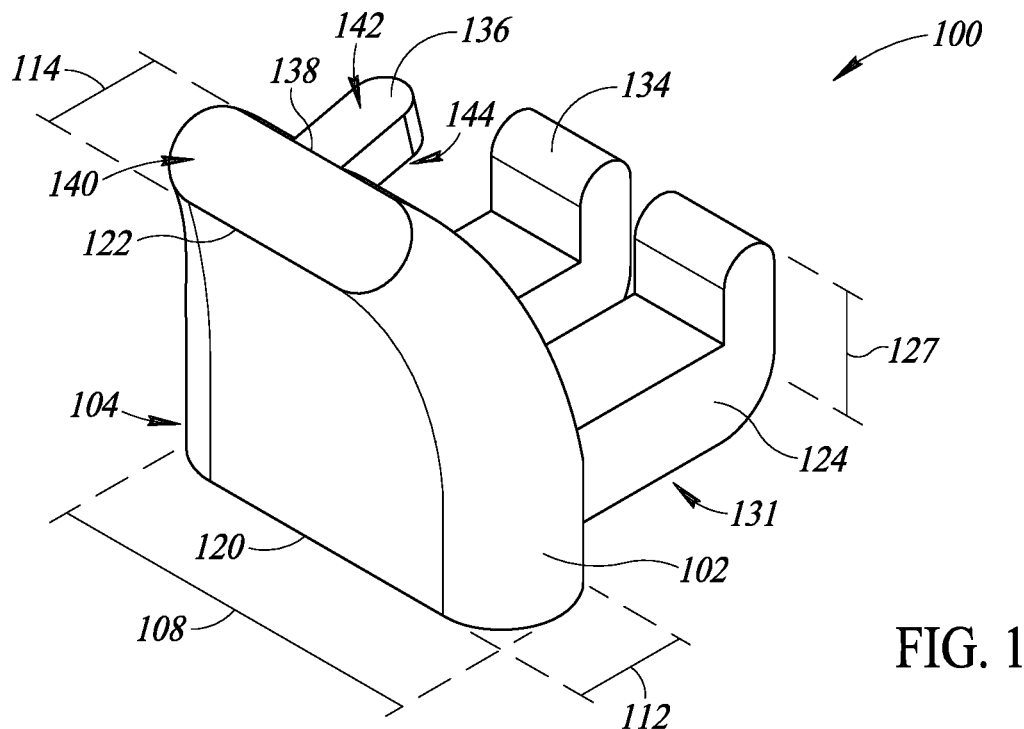
FIG. 1 is a rear perspective view of one or more embodiments of a brace according to the present disclosure.
Figure 2:
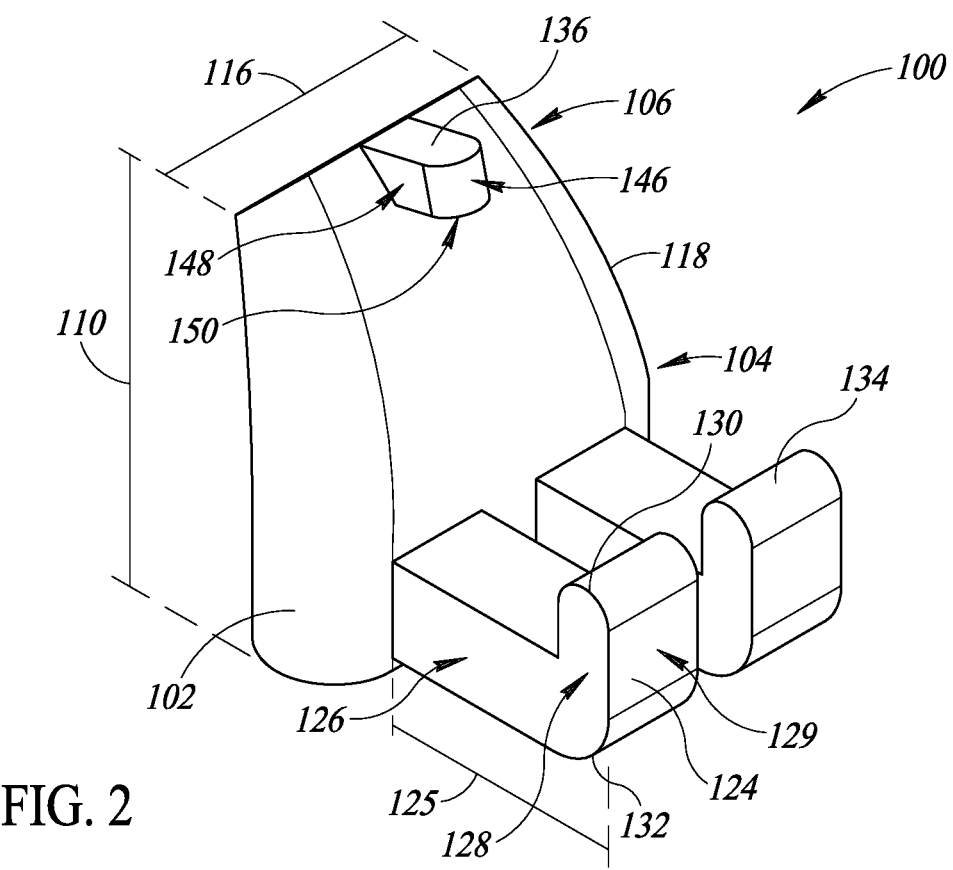
FIG. 2 is a front perspective view of the brace of FIG. 1.

FIGS. 1-2 illustrate one or more embodiments of a brace 100. In some embodiments, the brace 100 comprises a material suitable for 3D printing, such as acrylonitrile butadiene styrene (ABS), polylactic acid (PLA), polyamide (nylon), polyvinyl alcohol (PVA), glass filled polyamide, stereolithography materials (epoxy resins), alumide, silver, titanium, steel, sintered powdered metal, carbon fiber, photopolymers, or polycarbonate, among others. In other embodiments, the brace 100 comprises a plastic material, such as polypropylene or polyethylene, or a thermoplastic material, a polymer material, a metal or metal alloy, wood, or rubber, for example. The brace 100 includes a main body 102. The body 102 is a single, unitary, integral piece, however, in other embodiments, the body 102 may be multiple pieces coupled together, such as a first portion coupled to a second portion. In one or more embodiments, the single piece body 102 includes a first portion 104 and a second portion 106, which are a lower portion and an upper portion, respectively, of the main body 102. Alternatively, the first portion 104 may be a base or bottom portion and the second portion 106 may be a top portion. Still further, the first portion 104 may be a base portion and the second portion 106 may be a curved portion.

The body 102 has a first width 108 at a bottom region and a second width 116 at a top region. In one or more embodiments, the bottom region is the first portion 104 and the top region is the second portion 106. In one or more embodiments, the first width 108 is different than the second width 116. More specifically, the first width 108 is greater than the second width 116. The change in width of the brace 100 over the height 110 of the brace 100 is a continuous taper beginning at the first or bottom portion 104 such that sides 118 of the body are curved, although other configurations are contemplated in the present disclosure, such as a change in thickness that is a step down or step up configuration, a linear taper, a semi-circular taper, or others. In addition, the brace 100 has a first thickness 112 at the bottom region and a second thickness 114 at the top region. In one or more embodiments, the first thickness 112 and the second thickness 114 are equal or substantially equal, while in other embodiments, the first thickness 112 is greater than or less than the second thickness 114.

The brace 100 further includes a first protrusion 124 extending from the body 102. In an embodiment, the body 102 and the first protrusion 124 are a single, integral, unitary component, while in other embodiments, the first protrusion 124 is a separate component coupled to the body 102. The first protrusion 124 has a base 126 and a flange 128, respectively. In one or more embodiments, the base 126 is a first portion and the flange 128 is a second portion of the first protrusion 124. The base 126 has a length 125 between the body 102 and an outer surface 129 of the flange 128. The flange 128 has a height 127 between a base surface 131 of the first protrusion 124 and an outermost edge 130 of the flange 128 relative to base surface 131. In other words, the height 127 may be equal to a height of the flange 128 from the surface 131 to the first edge 130. In one or more embodiments, the length 125 is greater than the height 127, while in other embodiments, the length and height 125, 127 are equal or the height 127 is greater than the length 125.

The base 126 of the first protrusion 124 extends in a first direction relative to the body 102 and the flange 128 extends in a second, different direction to the body 102. In other words, the base 126 of the first protrusion 124 is transverse to the flange 128 of the first protrusion 124. In the illustrated embodiment, the base 126 and the flange 128 are perpendicular with respect to each other. The first protrusion 124 further includes the first edge 130 and a second edge 132, wherein each of the edges 130, 132 are rounded. In other embodiments, the edges 130, 132 are square, while in yet further embodiments, the edges 130, 132 are chamfered or at an angle to each other. The rounded edges 130, 132 assist with seating the first protrusion 124 in an aperture of an anchor, as described below.

The brace 100 further includes a second protrusion 134. In one or more embodiments, the second protrusion 134 may be identical to the first protrusion 124 and as such, certain features of the second protrusion 134 have not been repeated in the interest of brevity and to avoid obscuring details of the embodiments. In other embodiments, the second protrusion 134 is different than the first protrusion 124, for example in terms of size, shape, or with respect to edges 130, 132, among other things. The second protrusion 134 is spaced from the first protrusion 124, such that a portion of the anchors described below can be received between the protrusions 124, 134 in order to provide lateral stability to the protrusions 124, 134 and the brace 100 relative to the anchor. In an embodiment, the first protrusion 124 and the second protrusion 134 are each positioned equidistant relative to each other and sides 118 of the body 102 of the brace 100.

In other embodiments, such as in FIGS. 15-20, the brace 100 includes only one protrusion, such as the first protrusion 124, in which case, the protrusion 124 is positioned centrally with respect to the body 102 of the brace 100. In other words, in embodiments where there is only one protrusion, such as first protrusion 124, a distance between the sides 118 and a centerline through the protrusion 124 is equal. In yet further embodiments, the first protrusion 124 and the second protrusion 134 are combined into a single protrusion, in which case, there is no space between the protrusions 124, 134, but rather, the protrusions 124, 134 are a single, unitary, integral component approximately twice the size of either the illustrated protrusions 124, 134 with a generally similar shape as the protrusions 124, 134.

FIGS. 1-2 further illustrate that in one or more embodiments, the body 102 is at an angle, in other words, the body 102 and sides 118 are curved along the height 110 of the body 102 such that an outermost edge 122 of the top region is in a different vertical plane than an outermost edge 120 of the bottom region. In some embodiments the curve is away from the protrusions 124 and 134, while in other embodiments, it is towards the protrusions 124 and 134. The body 102 may also be straight.

The brace 100 further includes a third protrusion 136 coupled to and extending from the body 102 to receive a resilient connection member, as further explained below. It is to be understood that in embodiments where the brace 100 includes only one first protrusion, such as protrusion 124, the third protrusion 136 may generally be referred to as a second protrusion. In yet further embodiments, the third protrusion 136 is a second protrusion, and the second protrusion 134 is a third protrusion. The third protrusion 136 extends from the body 102 proximate the top region of the body 102. In some embodiments, the third protrusion 136 shares an edge 138 with a surface 140 bounded by the outermost edge 122 of the top region. As such, the third protrusion 136 is spaced from the first and second protrusions 124, 134 across the body 102 of the brace 100. The third protrusion 136 includes a first surface 142 opposite a second surface 144. Each of the first and second surfaces 142, 144 are flat and planar and in a spaced parallel relationship, although in other embodiments, the surfaces 142, 144 are rounded, curved, angled, or transverse with respect to each other.

A third surface 146 extends between the first and second surfaces 142, 144 of the third protrusion 136. The third surface 146 includes a first portion 148 integrated with, and transverse to, a second portion 150. In one or more embodiments, the first portion 148 is flat and planar and the second portion 150 is curved or rounded. In other embodiments, each of the portions 148, 150 are flat and planar or curved. In yet further embodiments, the portions 148, 150 are rectilinear and perpendicular to each other. The third protrusion 136 extends from the body 102 equidistant to sides 118 of the body 102 in one or more embodiments, such that force (e.g. tension) applied to the third protrusion 136 will be distributed equally throughout the brace 100. In an embodiment, the third protrusion 136 is aligned with the space between the first and second protrusions 124, 134. In other words, in an embodiment, a vertical center line defined by the third protrusion 136 would intersect a horizontal center line through the space between the protrusions 124, 134, wherein the horizontal center line through the space is equidistant to each of the first and second protrusions 124, 134.

Figure 3:
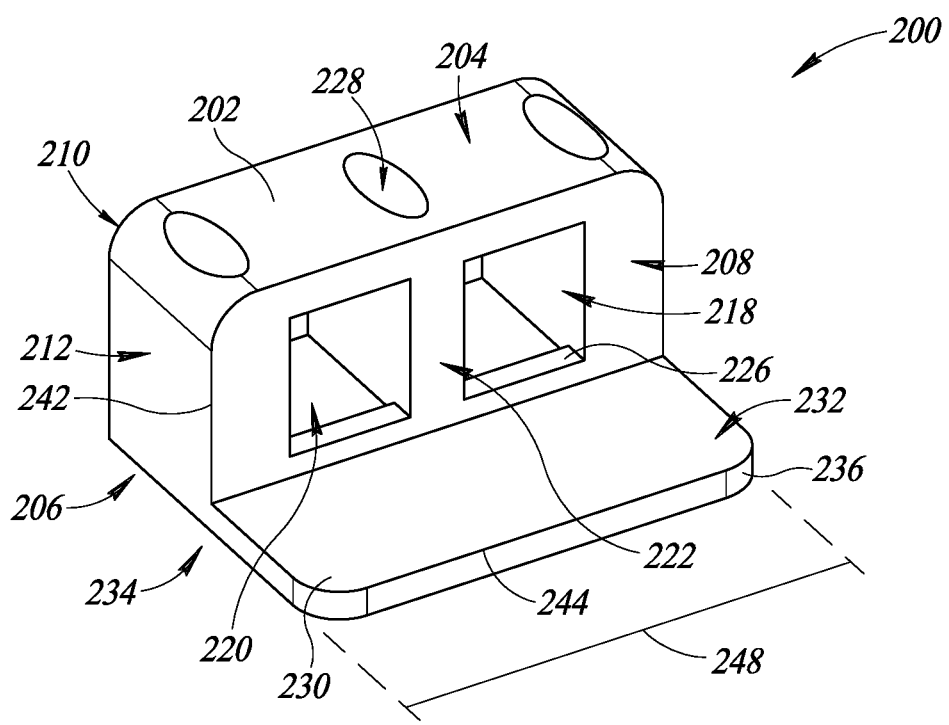
FIG. 3 is a front perspective view of one or more embodiments of an anchor according to the present disclosure.
Figure 4:
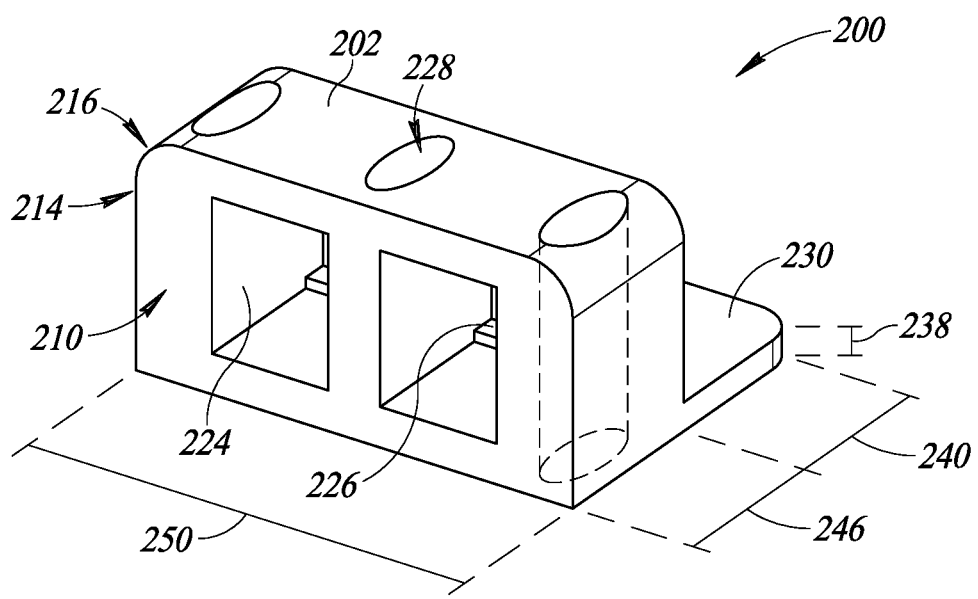
FIG. 4 is a rear perspective view of the anchor of FIG. 3.

FIGS. 3-4 illustrate one or more embodiments of an anchor 200. The anchor 200 can be formed from any of the materials provided above with respect to brace 100. In other embodiments, the anchor 200 may be referred to as a base, a device, an element, a fastener, or simply a body. The anchor 200 includes a body 202 having a first surface 204 opposite a second surface 206 and a third surface 208 opposite a fourth surface 210. The body 202 further includes a fifth surface 212 opposite a sixth surface 214, wherein the fifth surface 212 and the sixth surface 214 extend between the first and second surfaces 205, 206. In one or more embodiments, the first surface 204 is a top or upper surface, the second surface 206 is a bottom or lower surface, the third surface 208 is a front surface, the fourth surface 210 is a back or rear surface, the fifth surface 212 is a left surface and the sixth surface 214 is a right surface. Each of the second, third and fourth surfaces 206, 208, 210 are flat and planar. In addition, each of the first, fifth, and sixth surfaces 204, 212, 214 have a flat and planar portion joined together by rounded edges 216. In other words, each of the first, fifth, and sixth surfaces 204, 212, 214 include a flat and planar portion and at least one rounded or curved portion.

A first aperture 218 extends through the body 202 from the third surface 208 to the fourth surface 210 and a second aperture 220 extends through the body 202 from the third surface 208 to the fourth surface 210. The apertures 218, 220 are spaced from one another by a portion 222 of the body 202 extending between the apertures 218, 220. When the brace 100 (FIG. 1) is coupled to the anchor 200, the portion 222 is removably received in the space between the protrusions 124, 134 of the brace 100 (FIG. 1). As illustrated, each of the apertures 218, 220 are square or rectangular in shape with four sidewalls 224 defining each aperture 218, 220. In one or more embodiments, each of the sidewalls 224 are flat and planar and transverse relative to adjacent sidewalls 224. More specifically, each of the sidewalls 224 are perpendicular to adjacent sidewalls 224. However, in other embodiments, the apertures 218, 220 can have different shapes, such as a triangle shape, a circle shape, an oval shape, a trapezoid shape, or an irregular polygon shape. As such, the number of sidewalls 224 and their arrangement relative to each other may be different in other embodiments. Still further, each of the apertures 218, 220 may have the same size and shape, as in FIGS. 3-4, or may have different sizes and shapes relative to each other.

As will be described further, each of the apertures 218, 220 has a size and a shape to removably receive a respective protrusion of the brace 100 in FIGS. 1-2. More specifically, the first aperture 218 is configured to removably receive the first protrusion 124 of the brace 100 (FIG. 1) and the second aperture 220 is configured to removably receive the second protrusion 134 of the brace 100 (FIG. 1). In an embodiment, there is only one aperture, which may have the size of both apertures 218, 220 combined, or may be the size of only one of the apertures in order to receive a single protrusion of the brace 100 (FIG. 1). In such an embodiment, the single aperture aligns with the single protrusion of the brace 100 (FIG. 1) and more specifically, the single aperture is centrally disposed relative to the body 202 (e.g. spaced equidistant from the fifth surface 212 and the sixth surface 214).

Each of the apertures 218, 220 includes a ridge 226 extending between sidewalls 224 defining the apertures 218, 220. As such, the ridges 226 extend across each aperture 218, 220 between sidewalls 224 of each respective aperture 218, 220. Due to the ridge, the opening of each aperture 218, 220 in the third surface 208 has a smaller area than the opening of each aperture 218, 220 in the fourth surface 210. The ridge 226 assists with tilting the brace 100 (FIG. 1) to lock the brace 100 (FIG. 1) in place with the anchor 200. Other embodiments do not include a ridge 226, such as in FIG. 5, in which case the brace 100 (FIG. 1) can be held in place relative to the anchor 200 by the protrusions 124, 134 of the brace 100 (FIG. 1), by a friction fit, or by a light adhesive, for example.

In one or more embodiments, the body 202 further includes at least one hole 228 extending through the body 202 from the first surface 204 to the second surface 206, as indicated by dashed lines. In one or more embodiments, there are three holes 228, which may also be referred to as a plurality of holes 228. The center hole 228 extends through the body 202 through the portion 222 between the apertures 218, 220 while the outer two holes 228 extend through the body 202 on opposite sides of the apertures 218, 220. In other embodiments, there may be only one hole 228, or more or less than three holes 228. It is also possible for the holes 228 to extend through the apertures 218, 220, in which case, the holes 228 would align with corresponding holes on the protrusions 124, 134 of the brace 100 (FIG. 1). As discussed in further detail below with reference to FIG. 8, the at least one hole 228 provides airflow to the second surface 206 to assist with curing adhesive applied to the second surface 206. In other embodiments, such as in FIG. 5, the anchor 200 does not include holes, but rather, the adhesive cures without the additional airflow provided by the holes 228.

The anchor 200 further includes a flange 230 coupled to and extending from the third surface 208 of the body 202. In one or more embodiments, the flange 230 and the body 202 are a single, integral, unitary component comprising the anchor 200. In other embodiments, the flange 230 is a separate and distinct component coupled to the body 202. The flange 230 has a first surface 232 opposite a second surface 234, which are flat and planar. The second surface 234 is integral with the second surface 206. In other words, a bottom surface of the body 202 includes the surface 206 and the surface 234 as a single surface. When the anchor 200 is coupled to a nail of a user, the flange 230 acts as a fulcrum to apply torque to the nail. In other words, due to the force applied to the anchor 200 by the resilient connection members and braces described herein, the anchor 200 will tend to want to rotate about an edge 244 of the flange 230. As such, the flange 230 acts a fulcrum to apply a generally upward force to the nail to draw the nail, which is ingrown on at least one side, from the skin beneath the nail (see FIGS. 11-12). The second surface 206 of the body 202 receives adhesive to couple the anchor 200 to the nail, as described with reference to FIG. 8. In one or more embodiments, adhesive is also applied to a portion of the flange 230 to provide additional surface area to increase the bond strength between the nail, the adhesive, and the anchor 200. The second surface 206 of the body 202 may include small depressions or cavities or otherwise be provided with a rough surface texture for increasing the surface area, and therefore adhesion, of the second surface 206 to the nail via the adhesive.

Each of the first and second surface 232, 234 of the flange 230 are flat and planar with at least one rounded edge 236. Moreover, the first and second surfaces 232, 234 are parallel, meaning that a plane containing the first surface 232 of the flange 230 is parallel to a plane containing the second surface 234 of the flange 230. As such, the flange 230 is illustrated as having a thickness 238 between the first surface 232 and the second surface 234 that is constant or equal across the flange 230. However, in other embodiments, the flange 230 may taper, such that the thickness 238 may change across the flange 230, such as when the first surface 232 is transverse to the second surface 234 or when the first surface 232 is at a non-zero angle relative to the second surface 234. In yet further embodiments, one of the first and second surfaces 232, 234 includes a step down or step up configuration featuring an abrupt change in the thickness 238 similar to a step.

The flange 230 further includes a width 240. In one or more embodiments, the width 240 is from an edge 242 defining the third surface 208 of the body 202 to an edge 244 defining the first surface of the flange 230. The body 202 further includes a width 246. In one or more embodiments, the width 246 is between the edge 242 and the fourth surface 210, which corresponds to a width of the body 202. The widths 240, 246 of the flange 230 and the body 202 are equal, meaning that a width of the flange 230 and a width the body 202 are equal. In one or more embodiments, the first dimensions 240, 246 are different, such as the dimension 240 of the flange being more or less than the dimension 246 of the body 202.

Further, the flange 230 includes a length 248. In one or more embodiments, the length 248 is between the fifth and sixth surfaces 212, 214 of the body 202. The body 202 further includes a length 250. In some embodiments, the width 250 is between the fifth and sixth surfaces 212, 214 of the body 202. In further embodiments, the length 248 of the flange 230 is equal to the length 250 of the body 202, while in other embodiments, the lengths 248, 250 are different, such as the length 248 of the flange 230 being greater than or less than the length 250 of the body 202. The widths 240, 248 of the flange 230 and the lengths 246, 250 of the body 202 may be selected according to the desired bonding strength of the anchor 200 to the nail or to vary the torque applied to the nail, for example.

Figure 5:
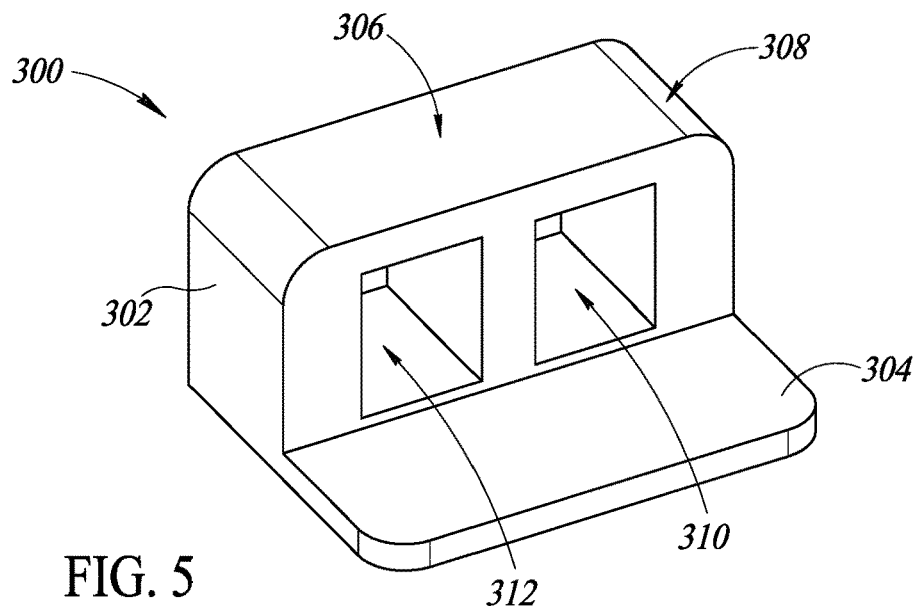
FIG. 5 is a front perspective view of one or more embodiments of an anchor according to the present disclosure.

FIG. 5 illustrates one or more embodiments of an anchor 300 according to the present disclosure. In some embodiments, certain features of the anchor 300 are the same as the anchor 200, and as such, those repetitive features will not be repeated in the interest of brevity and to avoid obscuring the details of the described embodiments. The anchor 300 includes a body 302 and a flange 304 extending from the body 302. The body 302 includes a top or upper surface 306, similar to the first surface 204 of the anchor 200 (FIG. 2). The surface 306 of the anchor 300 is flat and planar with opposite rounded edges 308. The surface 306 does not include any holes, apertures, or cavities extending there through, in one more embodiments. In other words, one embodiment of the anchor 300 does not include the holes 228 discussed above with reference to FIGS. 3-4. Rather, adhesive applied to the anchor 300 is able to cure without additional airflow provided by holes through the body 302. The anchor 300 further includes apertures 310, 312. However, apertures 310, 312 do not include ridges extending across the apertures 310, 312 between sidewalls of the apertures 310, 312. Rather, the apertures 310, 312 include openings on both sides of the body 302 that are equal in size and shape.

Figure 6:
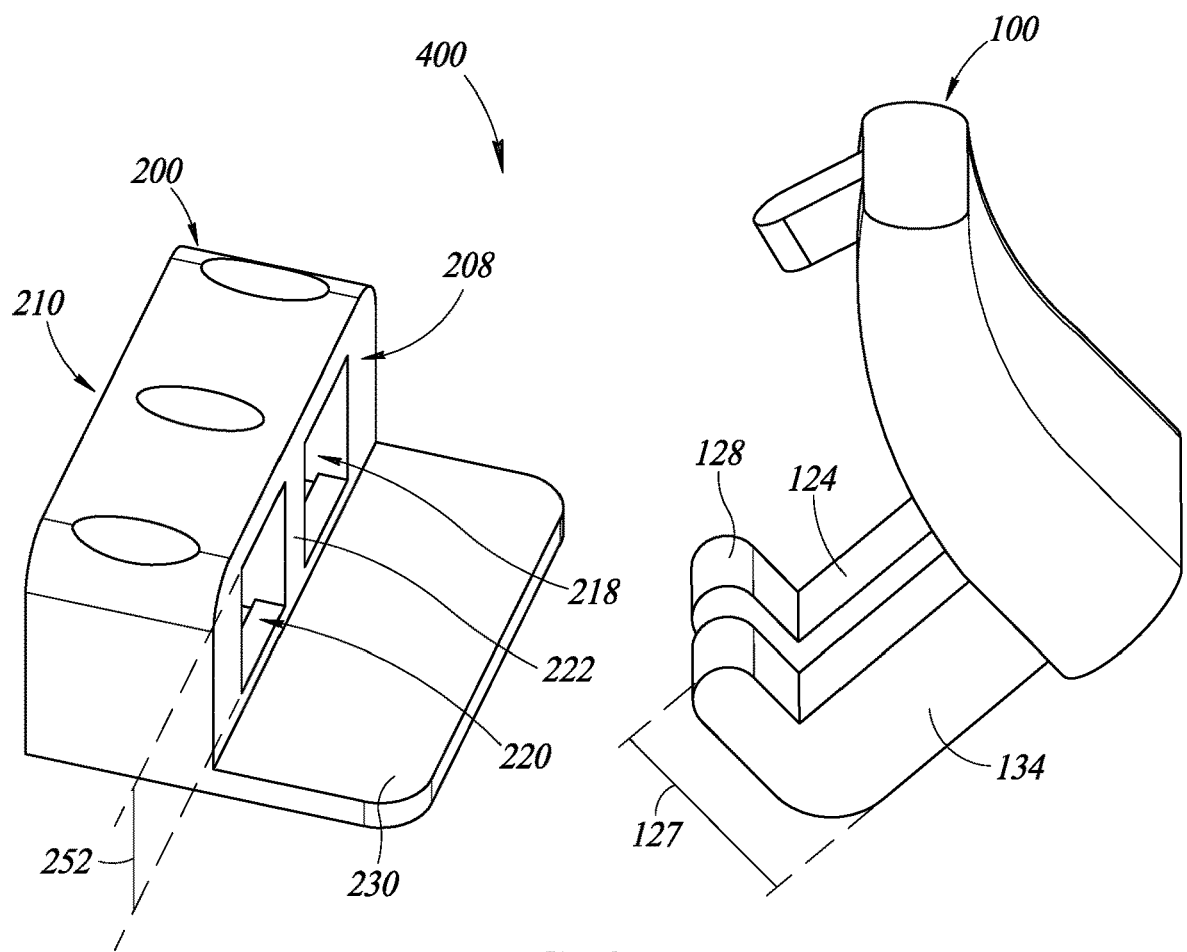
FIG. 6 is a perspective view of one or more embodiments of a system for correcting an ingrown nail according to the present disclosure illustrating a brace and an anchor in an uncoupled configuration.

FIG. 6 illustrates one embodiment of the full system 400 for correcting an ingrown nail. The system 400 includes an anchor 200 and a brace 100. In some embodiments, the anchor 200 can be same as anchor 300 described with reference to FIG. 5 and the brace 100 can be similar to the brace used in the system 500 of FIGS. 15-20. It is to be appreciated that the anchor 200 and the brace 100 may include such features described above with respect to the brace and anchor in FIGS. 1-5 even if not included the below description of system 400.

The anchor 200 includes the apertures 218, 220 extending through the anchor 200. The brace 100 includes the protrusions 124, 134 extending from the brace 100. In some embodiments, the brace 100 may be referred to as a lever, a body, a device, an element, a torque distribution element, or a force distribution element and the protrusions 124, 134 may be referred to as arms, lever arms, elements, or flanges.

The protrusions 124, 134 of the brace 100 are in spaced relationship. As illustrated in FIG. 6, the anchor 200 and the brace 100 are in an uncoupled configuration. In other words, the anchor 200 and the brace 100 are separate and distinct components of the system 400 that are configured to be coupled to each other, as described with reference to FIG. 7. Each of the apertures 218, 220 of the anchor 200 are sized and shaped to receive a respective protrusion 124, 134 of the brace 100. Put another way, each of the protrusions 124, 134 which may each be referred to as first protrusions of the brace 100, have a size and a shape such that they are configured to be positioned within a respective aperture 220 of the anchor 200.

Each of the protrusions 124, 134 further includes a flange 128, which may also be referred to as a foot, a securing element, or a locking element. The anchor 200 further includes the surface 208 opposite the surface 210, which are referred to as the third surface and the fourth surface, respectively, in FIGS. 3-4. The apertures 218, 220 extend through the anchor 200 from the surface 208 to the surface 210 such that the protrusions 124, 134 of the brace 100 can be inserted through the anchor 200. As described above, the anchor 200 further includes the portion 222 between the apertures 218, 220 such that the apertures 218, 220 are spaced apart by the portion 222. Each of the flanges 128 of the protrusions 124, 134 further includes the height 127 and each of the apertures 128, 220 further includes a height 252. The height 127 is greater than the height 252 such that the flanges 128 secure the brace 100 in position relative to the anchor 200 once inserted through the apertures 218, 220. In other words, the flanges 128 prevent the brace 100 from uncoupling with the anchor 200 by a lateral force because the flanges 128 are larger than the apertures 218, 220.

Figure 7:
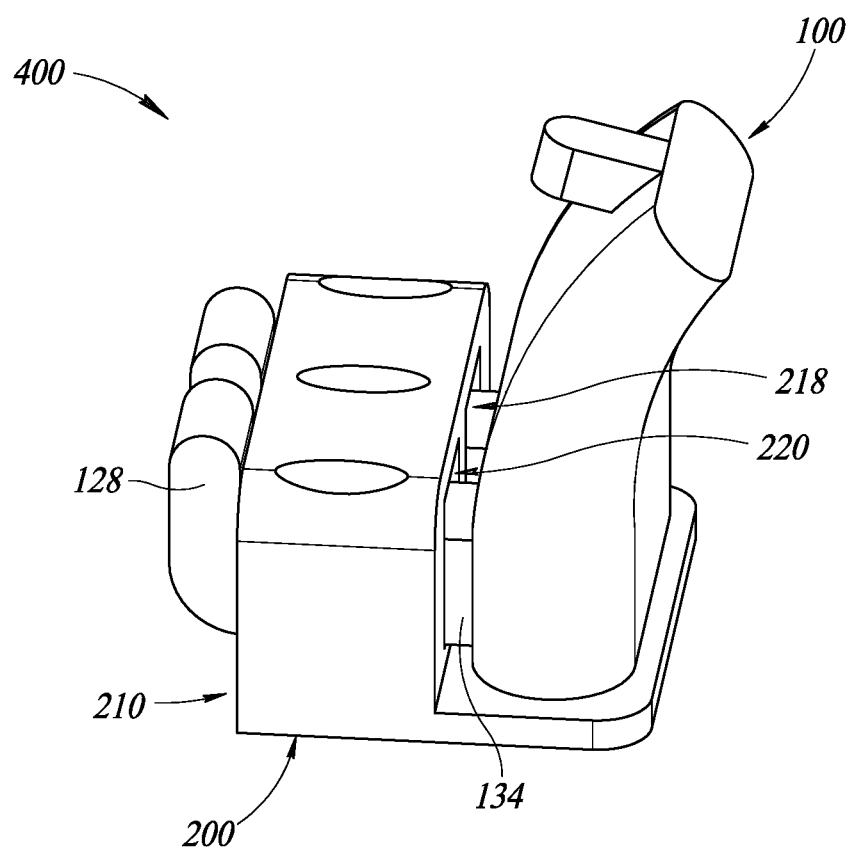
FIG. 7 is a perspective view of the system of FIG. 6 illustrating the brace and the anchor in a coupled configuration.

FIG. 7 illustrates the anchor 200 and the brace 100 in a coupled configuration with the protrusions 124, 134 of the brace 100 removably positioned in the apertures 218, 220 of the anchor 200. In operation, a user inserts the protrusions 124, 134 of the brace 100 into the apertures 218, 220 of the anchor 200 by first tilting the brace 100 such that the flanges 128 of each protrusion 124, 134 are guided through the respective apertures 220 of the anchor. In other words, the brace 100 is rotated away from the flange 230 of the anchor 200 and manipulated towards the anchor 200 such that the flange 128 of each protrusion 124, 134 extend through the apertures 218, 220 of the anchor 200. Then, after the flanges 128 of the protrusions 124, 134 of the brace 100 are guided through the apertures 218, 220 of the anchor 200, the user rotates the brace 100 back towards the flange 230 of the anchor 200 while continuing to manipulate the brace 100 towards the anchor 200. This series of actions results in the brace 100 coupled to the anchor 200 with the protrusions 124, 134 extending through the apertures 218, 220. Moreover, the flanges 128 of the protrusions 124, 134 of the brace 100 are proximate the surface 210 of the anchor 200. In an embodiment, the flanges 128 are in abutting physical contact with the surface 210 of the anchor 200, while in other embodiments, there is a small space or gap between the flanges 128 and the surface 210 of the anchor 200.

FIG. 7 further illustrates the portion 222 of the anchor 200 extending between and separating the apertures 218, 220 of the anchor 200 received in the space between the protrusions 124, 134 of the brace 100. Moreover, because the height 127 of the flanges 128 of the brace 100 is greater than the height 252 of the apertures 218, 220 of the anchor 200, the flanges 128 of the brace 100 secure the brace 100 to the anchor 200. Put another way, the flanges 128 prevent the brace 100 from uncoupling with the anchor 200. As will be described below, when a resilient connection member is coupled to the brace 100, the resilient connection member will produce a force on the brace 100 that tends to draw the brace 100 away from the anchor 200. In other words, the force from the resilient connection member tends to cause lateral movement of the brace 100 relative to the anchor 200, wherein the flanges 128 of the brace 100 prevent the brace 100 from uncoupling with the anchor 200 due to such force. In addition, the force from the resilient connection member tends to manipulate the brace 100 such that the protrusions 124, 134 rotate upwards relative to the anchor 200 and the flanges 128 assist in transferring the force to the anchor 200, such that the anchor 200 generates a similar upward torque on the nail to which the anchor 200 is coupled.

Figure 8:
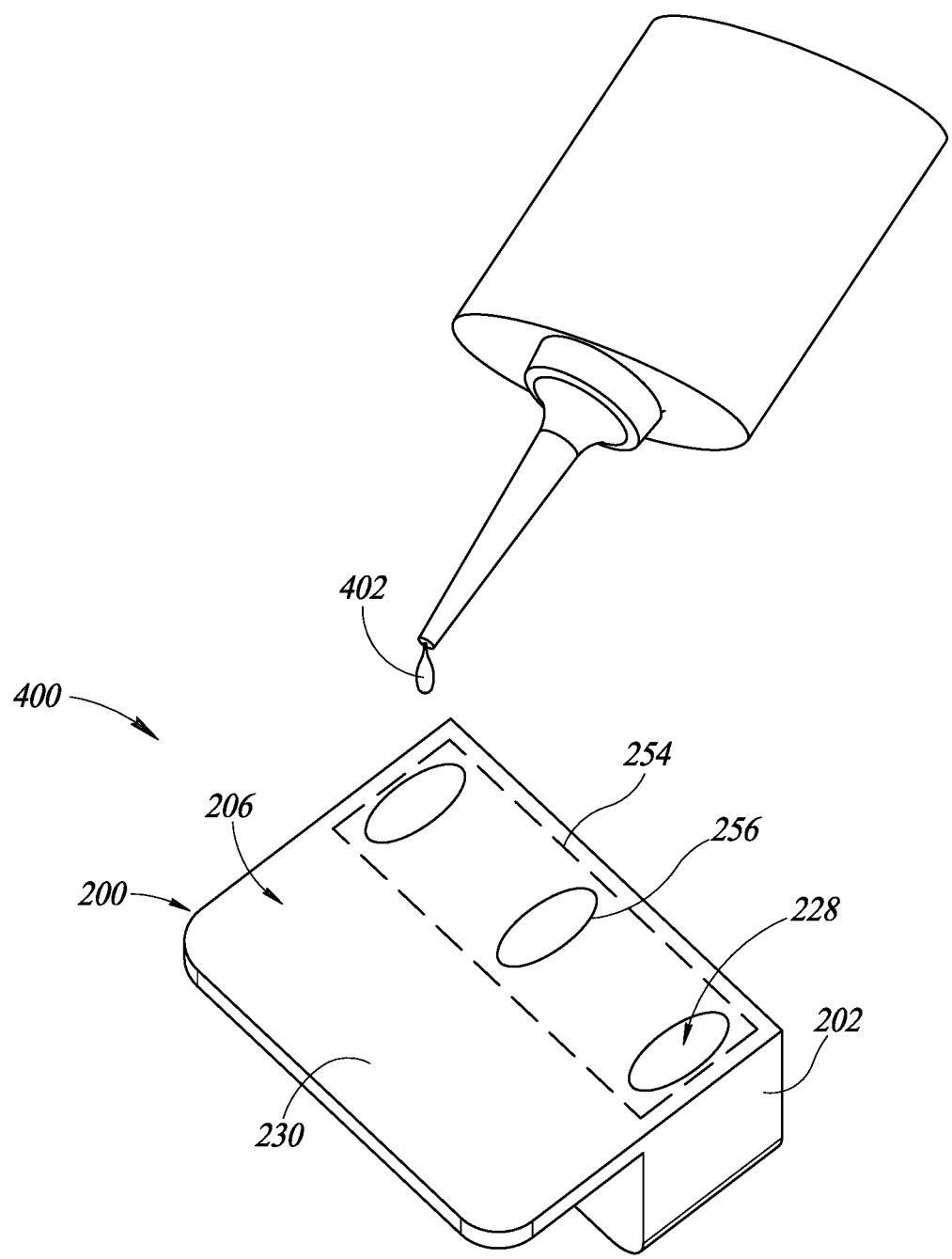
FIG. 8 is a bottom perspective view of the anchor of the system of FIG. 6 illustrating adhesive applied to the anchor.

FIG. 8 illustrates application of an adhesive 402 to the anchor 200 of the system 400. The anchor 200 includes the body 202 having the second surface 206. In one or more embodiments, the second surface 206 is a base or bottom surface of the anchor 200. Before coupling the brace 100 to the anchor 200, a user applies adhesive 402 to the second surface 206 of the anchor 200. Any suitable and commercially available adhesive may be used as the adhesive 402, such as nail glue. The adhesive 402 is applied to an area 254, indicated by dashed lines, of the second surface 206 that is less than an area of the entire second surface 206. In one or more embodiments, the area 254 is less than half of an area of the second surface 206. The area 254 generally corresponds to an area of the second surface 206 below a body 202 of the anchor 200 described with reference to FIGS. 3-4. Adhesive 402 is not applied to an area corresponding to the flange 230 of the anchor 200. However, in one or more embodiments, the adhesive 402 is applied to the entire area of the second surface 206, including the area 254 as well as the area corresponding to the flange 230. The anchor 200 further includes at least one hole 228 extending through the anchor 200. In the illustrated embodiment, there are a plurality of holes 228, with each hole having an opening 256 inside the area 254. The holes 228 provide airflow through the anchor 200 to assist with curing the adhesive 402. While the holes 228 are not required, as in FIG. 5, the embodiments of the anchor 200 that includes holes 228 generally enable curing of the adhesive 402 in less time than embodiments without the holes 228.

Figure 9:
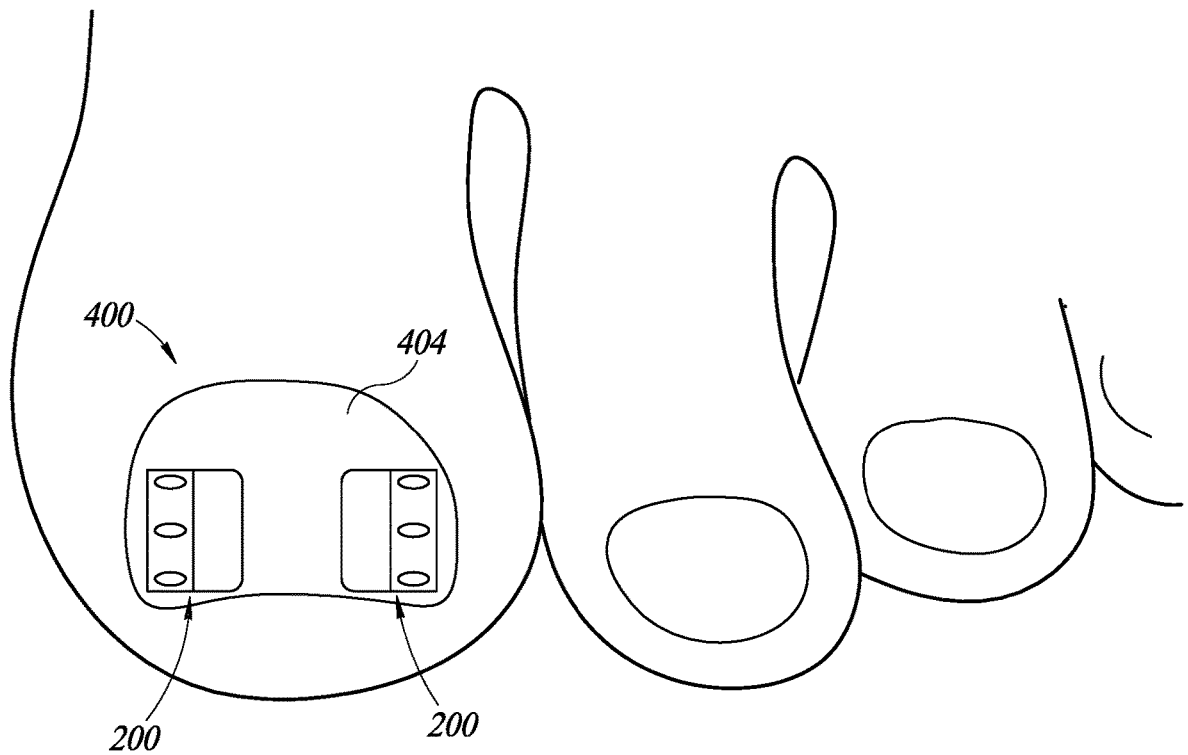
FIG. 9 is a top plan view of the anchor of FIG. 8 coupled to a nail of an end user.

FIG. 9 illustrates one or more embodiments of the anchors 200 of the system 400 coupled to a nail 404 of a user. More specifically, the system 400 includes two anchors 200, one for each side of the nail 404. After application of the adhesive 402 to both anchors 200 as in FIG. 8, but before coupling the braces 100 to the anchors as in FIG. 11, the anchors 200 are coupled to the nail 404 of the user. Coupling the anchors 200 to the nail 404 first allows the user to ensure that the anchors 200 are securely physically coupled to the nail 404 before proceeding with installation. In other words, in one or more embodiments, if the anchors 200 are not appropriately secured to the nail 404 after curing of the adhesive 402, the user can clean the anchors 200 and the nail 404 and reapply the anchors 200 to the nail 404 with the adhesive 402.

Figure 10:
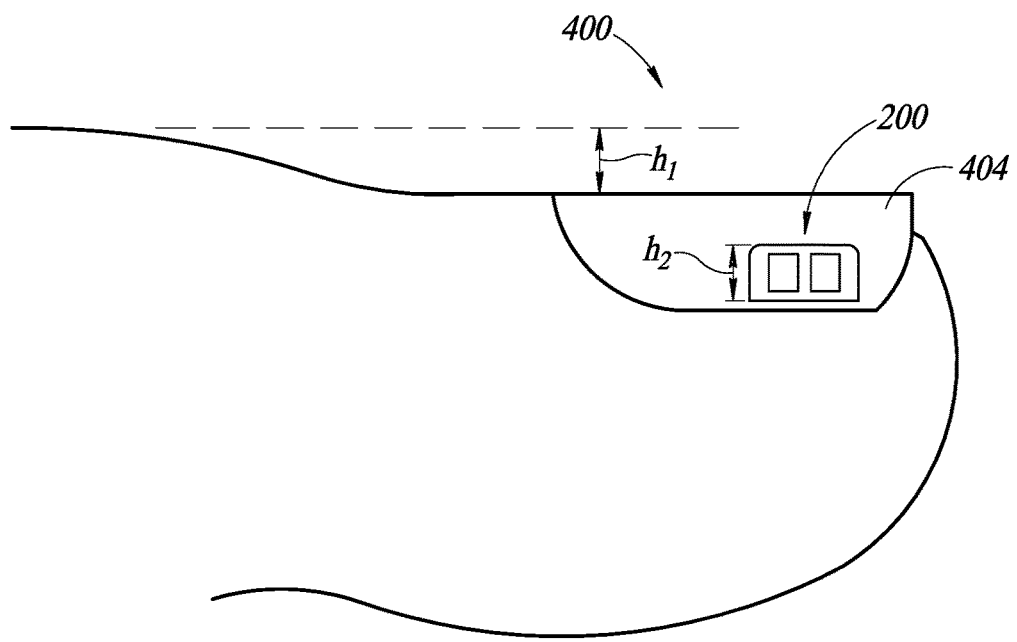
FIG. 10 is a side elevational view of the anchor of FIG. 8 coupled to a nail of an end user.

FIG. 10 illustrates a side view of the anchor 200 coupled to the nail 404. In this embodiment, the anchors 200 are low profile anchors. In other words, each anchor 200 has a height h2 relative to the nail 404 and the toe (or other appendage) of the user has a height h1 above the nail 404. As shown in FIG. 10, the height h2 of each anchor 200 is less than the height h1. Moreover, the braces 100 are removably coupleable with the anchors 200, as described herein. As such, the user can remove the braces 100 and the resilient connection member, leaving only the anchors 200 coupled to the nail 404. Because the height h2 of each anchor 200 is less than the height h1 of the toe relative to the nail, the user can remove the braces 100 and resilient connection member and comfortably wear socks and shoes over the anchors 200. In other words, embodiments of the anchor 200 described herein and the system 400 enable correction of ingrown nails without impacting the day to day activities of the user, the braces 100 can be removed from the anchors 200, and the anchors worn with normal shoes and socks in between treatments.

As such, a method of treatment according to the present disclosure includes connecting anchors 200 to locations on the nail 404, such as on the sides of a toe nail, coupling a brace 100 to each anchor 200, and coupling a resilient connection member (see FIG. 11) between the braces 100. Then, at a second time period, the resilient connection member (see FIG. 11) and the braces 100 can be removed and the anchors 200 worn with socks and shoes. At a third, later time period, the braces 100 and the resilient connection member (see FIG. 11) are re-attached to the anchors 200 and treatment is resumed. Moreover, treatment can include coupling a second resilient connection member with a different resilience (e.g., exerting a different amount of force when stretched to the same dimensions) than the first resilient connection member at any of the above time periods. As such, the resilience of the resilient connection member can be selected based on the status of treatment.

Figure 11:
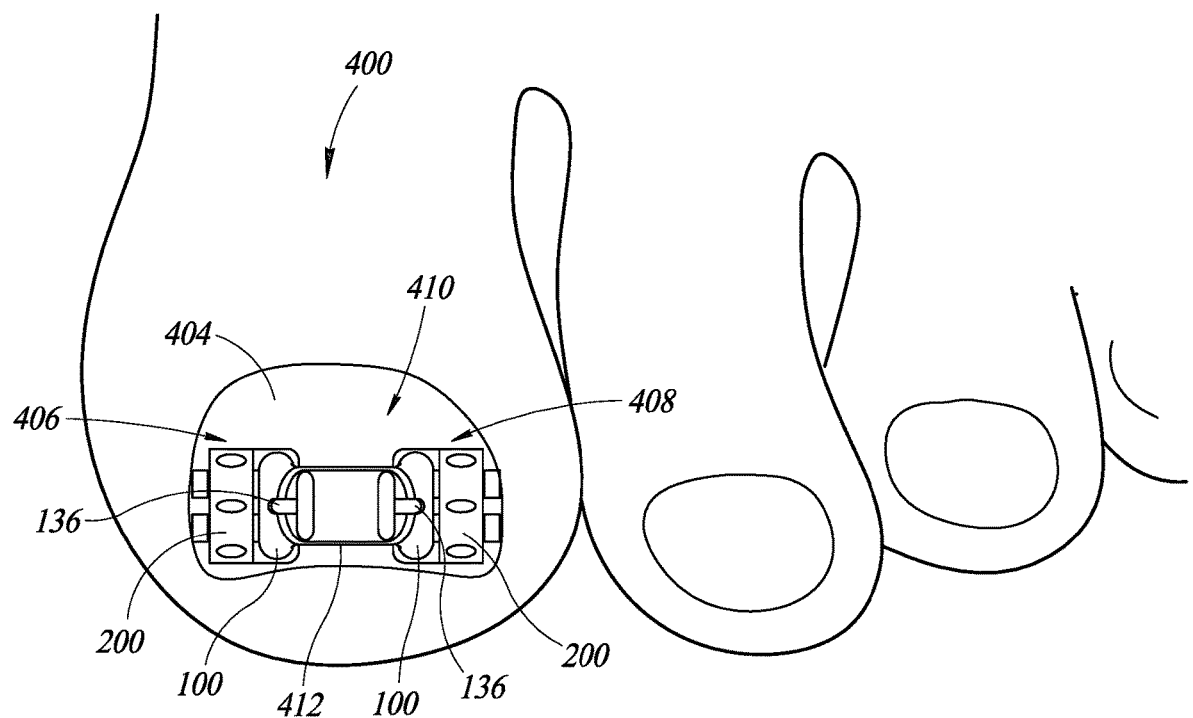
FIG. 11 is a top plan view of the system of FIG. 6 coupled to a nail of an end user with a resilient connection member coupled between the braces.

FIG. 11 illustrates the complete system 400 coupled to the nail 404 of the user, including both anchors 200 and both braces 100 coupled to the anchors 200. The nail 404 is a toe nail of a user's big toe. However, it is to be appreciated that the system 400 can be coupled to any of the nails of the user, such as any of the user's other toe nails or any of the user's finger nails that are suffering from an ingrown nail. The nail 404 is an ingrown nail. The system 400 includes the anchor 200 and the brace 100 coupled to a first side 406 of the nail 404. The anchor 200 and the brace 100 may be referred to as a first anchor and a first brace. The system 400 further includes the second anchor 200 and the second brace 100 coupled to a second side 408 of the nail 404 opposite the first side 406. In one or more embodiments, each of the anchors 200 are identical to anchor 300 in FIG. 5, while in other embodiments, each of the anchors 200 are identical to anchor 200 described with reference to FIGS. 3-4. In one or more embodiments, the anchor 200 and brace 100 pairs are replaced with the single piece nail correction devices 500 described with reference to FIGS. 15-20.

The system 400 includes two anchor and brace pairs (e.g. a first pair including anchor 100 and brace 220 and a second pair including anchor 200 and brace 100) positioned on opposite sides 406, 408 of the nail 404 of the user. Each of the anchors 200 are coupled to the nail 404 with the adhesive 402 described with reference to FIG. 8. In this embodiment, the braces 100 are coupled to the anchors 200 before application of the adhesive 402. In other words, the braces 100 and anchors 200 are assembled as a unit before application of the adhesive. However, the braces 100 remain removably coupled to the anchors 200, such that the braces 100 can be removed, and the anchors 200 worn with socks and shoes, as described with reference to FIGS. 9-10.

In one or more embodiments, before application of the anchors 200 to the nail 404, the user roughs a surface 410 of the nail 404 with sand paper, a pumice stone, or a nail file, for example, in order to improve the adhesive between the surface 410 of the nail 404, the adhesive 402 (FIG. 8) and the anchors 200. After the braces 100 are coupled to the anchors 200 and the anchors 200 are coupled to the nail 404, a resilient connection member 412 is coupled between the braces 100, 100. More specifically, the resilient connection member 412 is coupled to the protrusion 136 extending from the first brace 100 and the protrusion 136 extending from the second brace 100. As such, the resilient connection member 412 extends from the brace 100 to the brace 100. In one or more embodiments, the resilient connection member 412 is an elastic material in a loop, such as a rubber band for example. In some embodiments, the resilient connection member 412 is a loop of polymer, silicon, thermoplastic, or other material. The resilient connection member 412 exerts a force on the braces 100 to draw the anchors 200 towards each other.

More specifically, the resilient connection member 412 is elastic so as to provide a lateral force generally towards a center of the nail 404 between the anchors 200 and braces 100. An amount of force applied can be selected by replacing the resilient connection member 412 with an alternative resilient connection member with different resilient or elastic properties. For example, a first resilient connection member may have a first elasticity and resiliency and a second resilient connection member of the same size and shape may have a second, greater elasticity and a second, lesser resiliency due to a reduction in thickness of the material comprising the second resilient connection member. The first resilient connection member can be selected to generate generally more force on the braces 100 than the second resilient connection member. Any number of different resilient connection members can be selected for use with system 400 to generate the desired amount of force on the braces 100 and the system 400 generally.

Figure 12:
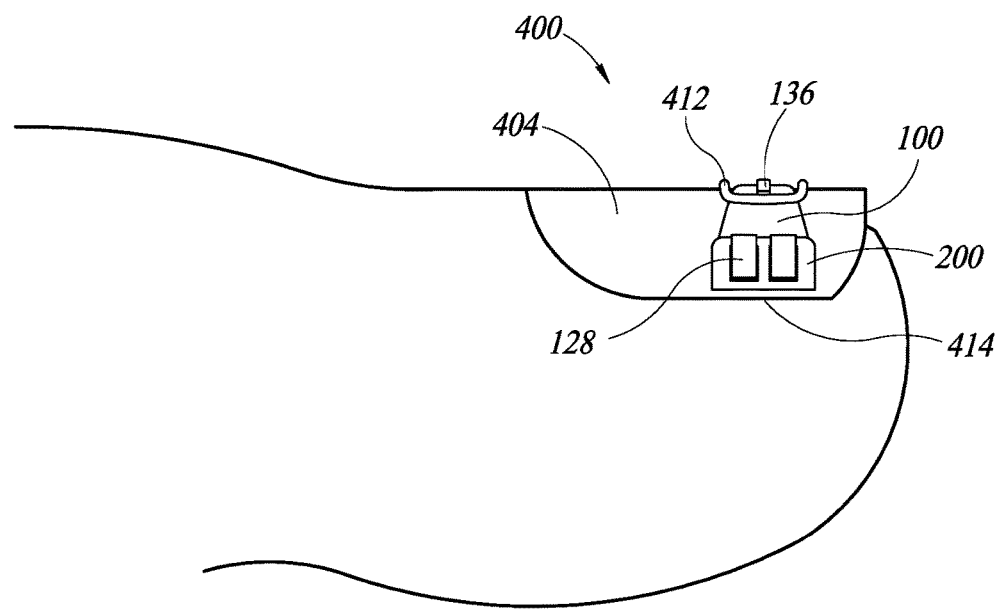
FIG. 12 is a side elevational view of the system of FIG. 9.

FIG. 12 illustrates a side view of the anchor 200 and brace 100 coupled to the nail 404 as well as part of the resilient connection member 412 coupled to the brace 100 via the protrusion 136. More specifically, the resilient connection member 412 is coupled beneath the protrusion 136. In one or more embodiments, the anchor 200 is positioned proximate an edge 414 of the nail 404, which may be an outermost edge of the nail 404. The flanges 128 of each of the protrusions 124, 134 408 (FIG. 6) extend through the anchor 200 and prevent the brace 100 from uncoupling with the anchor 200 as the resilient connection member 412 provides a lateral force (e.g. in a direction in and out of the page in the orientation shown) against the brace 100.

Figure 13:
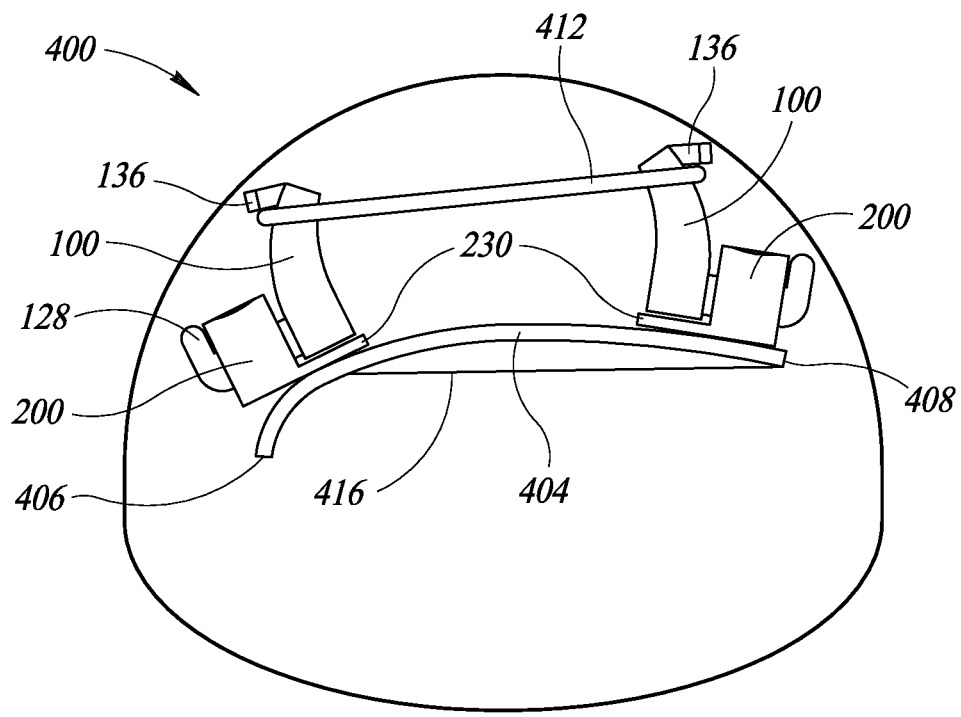
FIG. 13 is a front elevational view of the system of FIG. 6 coupled to an ingrown nail of an end user illustrating the nail in an ingrown configuration.
Figure 14:
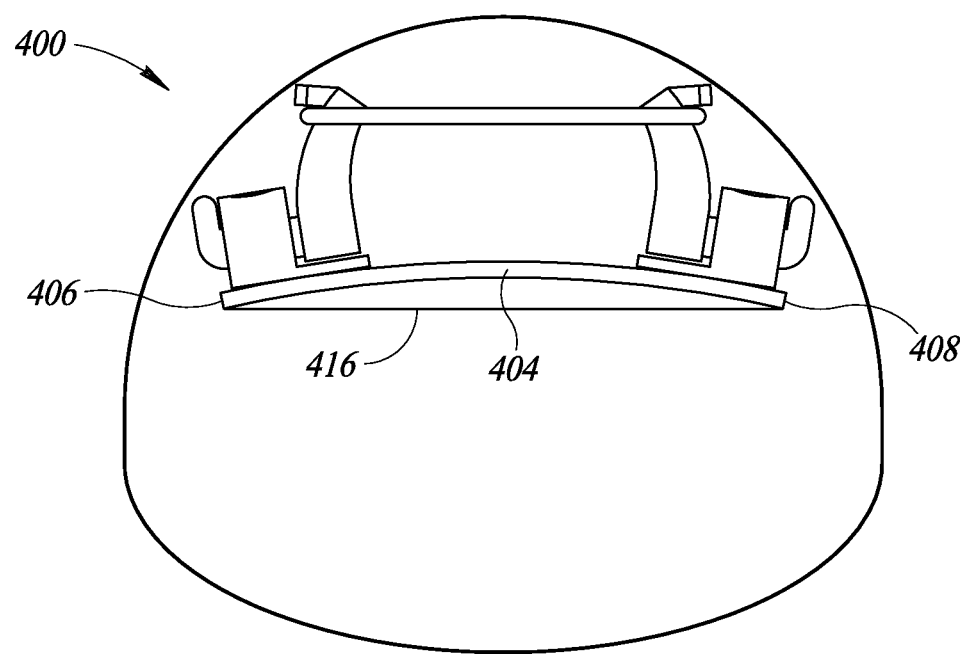
FIG. 14 is a front elevational view of the system of FIG. 13 illustrating the ingrown nail in a corrected configuration.
Figure 15:
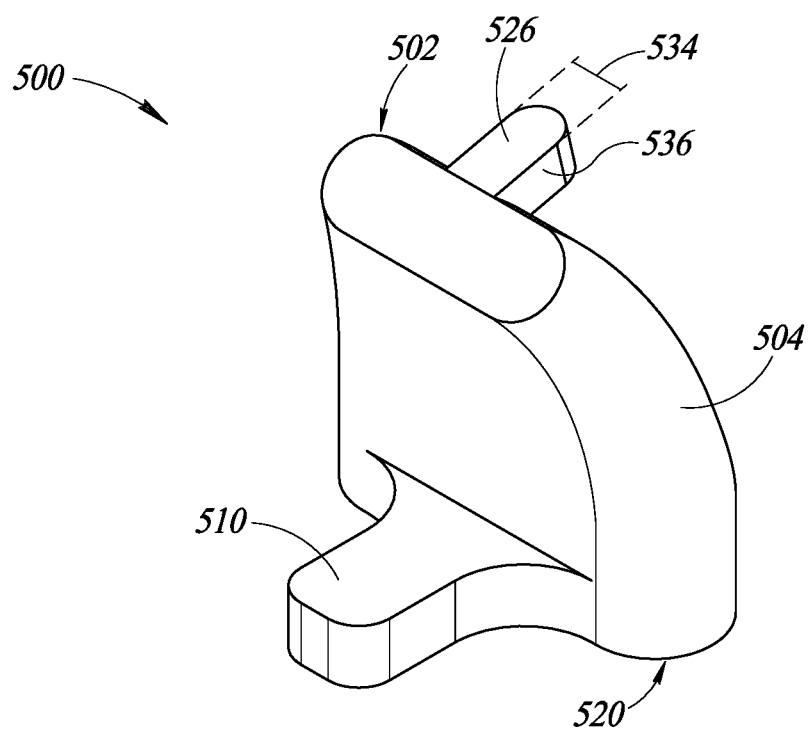
FIGS. 15-20 are views of one or more embodiments of a system for correcting an ingrown nail according to the present disclosure including a device configured to be coupled to a nail of a user with a protrusion for receiving a resilient connection member.
Figure 16:
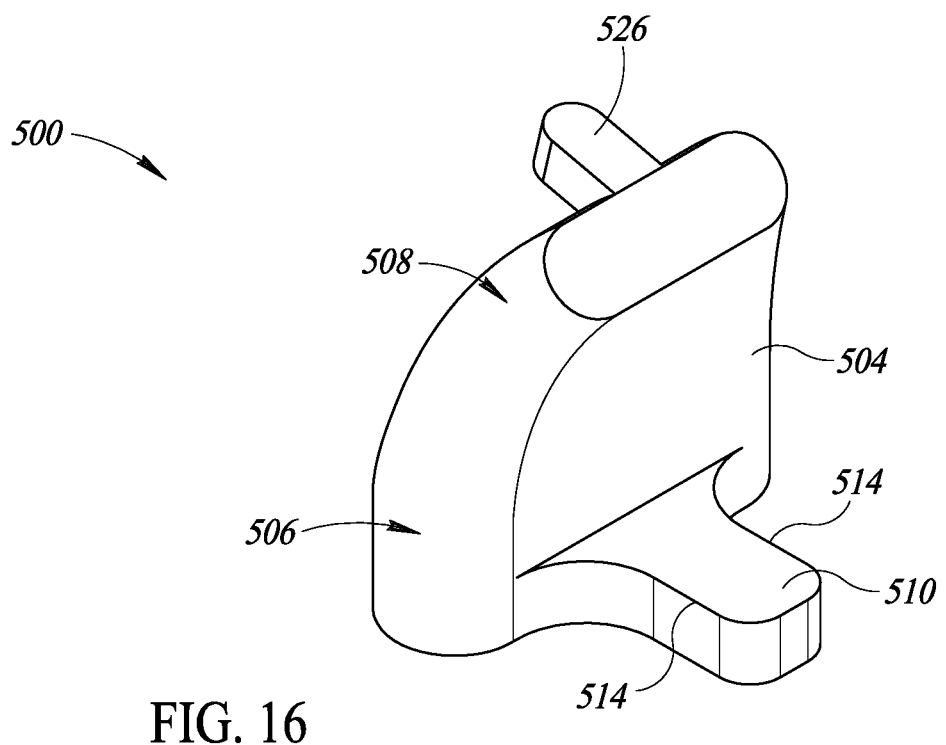

FIG. 13 illustrates the system 400 coupled to the nail 404, which is ingrown. In other words, the first side 406 of the nail 404 is curved and has grown into the nail bed 416 on which the nail 404 rests. The anchor 200 and the brace 100 are coupled to the nail 406 proximate the first, ingrown side 406 of the nail 404 and the anchor 200 and the brace 100 are coupled to second side 408 of the nail 406 opposite the first side 406. In operation, the resilient connection member 412 provides a force on each protrusion 136 of each brace 100 towards a center of the nail 404. The protrusions 136 distribute the force to the braces 100, which distribute the force to the anchors 200. The force on the braces 100 causes the flanges 128 and the protrusions 124, 134 of each brace 100 to want to rotate away from the respective anchors 200. As such, the force applied by the resilient connection member 412 generates torque on each anchor 200 via the braces 100.

This torque is transferred to the nail 404, which generally causes the nail 404 to move upwards back towards the nail bed 416. The torque generated by the system 400 is less than a torque required to remove the nail 404 from the nail bed 416 completely. Moreover, the generally curved shape of the body of each brace 100 assists with generating torque on the anchors 200 by changing the angle of the applied force from the resilient connection member 412 relative to the anchors 200 via the curved shape of the braces 100. In one or more embodiments, the bodies of the braces 100 are straight and rectilinear, in which case the torque will still be appropriately applied, although in such an embodiment, the torque may be more or less than the torque generated by the curved bodies of the braces 100. Still further, the flange 230 of each anchor 200 sits below the braces 100 to act as a fulcrum on which the braces 100 rest and pivot. In other words, the flanges 230 assist with transferring the force from the resilient connection member 412 into torque on the anchors 200.

Over time, the nail 404 returns to a corrected position, as in FIG. 12. In other words, the continuous application of tension from the resilient connection member 412 generates torque on the nail 404 that tends to pull the nail from the nail bed 416 and back to the position shown in FIG. 12, namely resting on the nail bed 416 in a non-ingrown or correct position. In the illustrated position, both of the sides 406, 408 of the nail 404 are in contact with the nail bed 416 but neither side 406, 408 is growing into the nail bed 416 beyond a standard amount for a non-ingrown nail. At this point, the system 400 can be removed from the nail 404 and any remaining adhesive 402 (FIG. 8) can be removed with a solvent to return the nail 404 to its original condition before installation of the system 400. In an embodiment, a treatment time for curing the ingrown nail 404 is less than 14 days, or less than 10 days, or even less than 7 days. In one or more embodiments, the treatment time is between 1 to 2 days.

FIGS. 15-20 illustrate one alternative embodiment of a system 500 for correcting an ingrown nail. Although FIGS. 15-20 illustrate one device 502 that is part of the system 500, it is to be appreciated in light of the discussion above that a second device that is identical to device 502 is part of the system 500, the details of which have been omitted for brevity and to avoid obscuring the features of the embodiment of the system 500.

FIGS. 15-20 illustrate the device 502 having a body 504 with a first portion 506 integral with a second portion 508. In an embodiment, the first portion 506 is a base or lower portion and the second portion 508 is a curved portion or upper portion. The body 504 further includes a first protrusion 510 extending form the body 504 proximate the first or base portion 506. A width 512 of the first protrusion 510 between outer edges 514 of the first protrusion 510 is less than a width 516 of the body 504 between outer edges 518 of the body 504. The body 504 further includes a surface 520, which is a base or bottom surface in an embodiment, which is configured to be coupled to a nail 524 of a user with an adhesive 522, as in FIG. 19. As such, the surface 520, which is a surface of the body 504 and the first protrusion 510, may generally be referred to as an outermost surface or a surface configured to be coupled to the nail 524 of the user.

A second protrusion 526 extends from the second or curved portion 508 of the body 504. The second protrusion 526 may be similar to the third protrusion 136 described with reference to FIGS. 1-2. The second protrusion 526 and the body 504 define a recess or cavity 528 for receiving a resilient connection member, such as resilient connection member 412 in FIGS. 11-14. As illustrated more clearly in FIG. 19, the first protrusion 510 extends from the body 504 in a first direction and the second protrusion 526 extend from the body 504 in a second, different direction, such that the first direction is transverse to the second direction.

In operation, a user applies adhesive 522 to the surface 520 and attaches the surface 520, and thus the device 502 to the nail 524, similar to the process described above with reference to FIGS. 1-12. The surface 520 is flat and planar. As with the system 400 described with reference to FIG. 8, the adhesive 522 is applied to the surface 520 in an area that corresponds to the body 504. In other words, adhesive 522 is not applied to a portion of the surface 520 corresponding to the first protrusion 510. As such, in operation, the first protrusion 510 acts as a fulcrum to distribute force or torque to the nail, similar to flanges 230 described with reference to FIG. 13. More specifically, the force on the body 504 via the resilient connection member (such as resilient connection member 412 in FIG. 11) tends to bias the body 504 to the left in the orientation shown in FIG. 19. However, because the body 504 is coupled to the nail 524, the force is converted to torque applied to the nail 524, wherein the body 504 tends to want to rotate about point 530 proximate the first protrusion 510. As such, the first protrusion 510 acts as a fulcrum and the body 504 as a lever, to assist with raising the nail 524 from an ingrown position to a corrected position.

Figure 17:
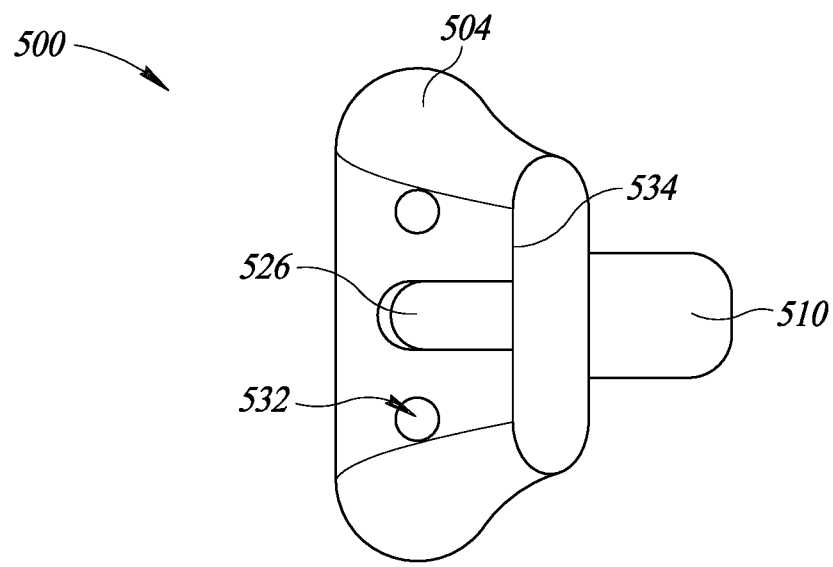
Figure 18:
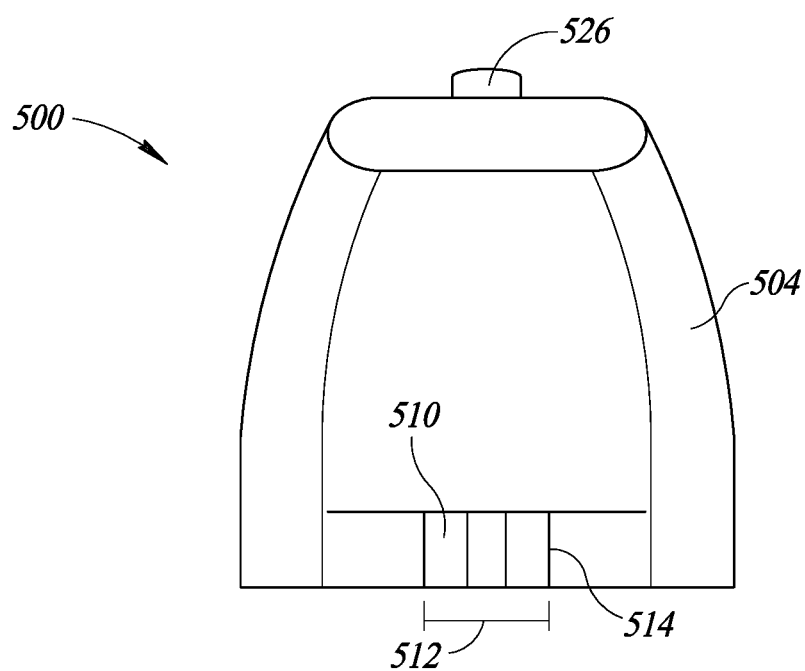
Figure 19:
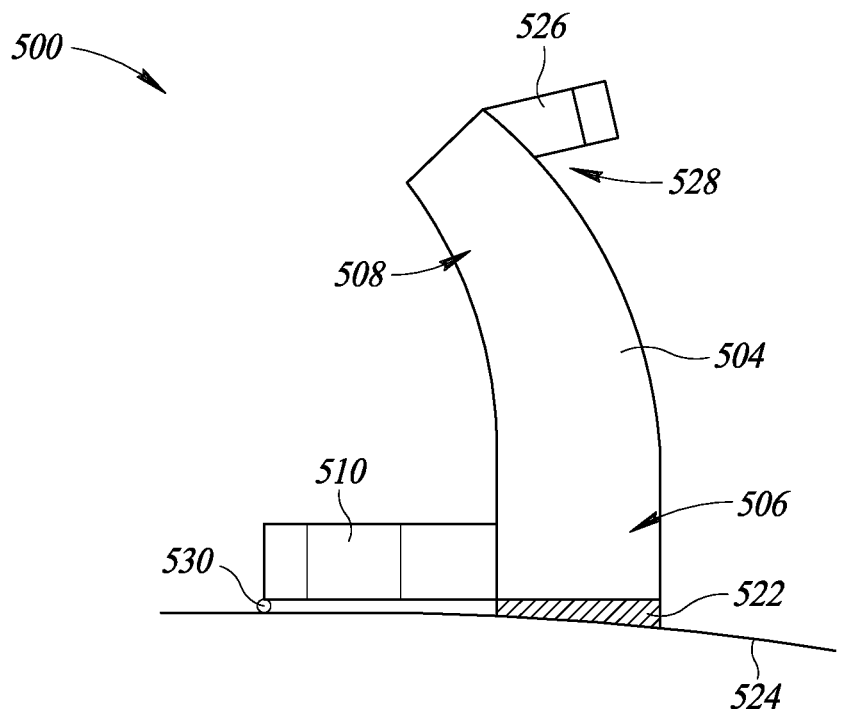
Figure 20:
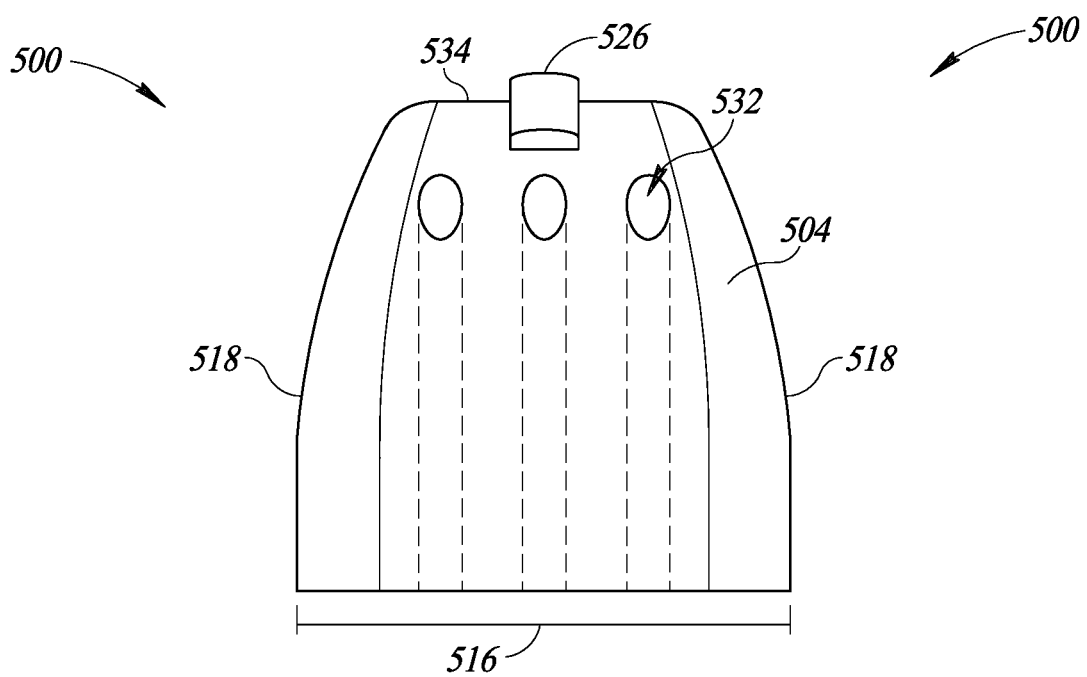

FIGS. 17 and 20 further illustrate the body 504 having a plurality of holes 532 extending through the body 504 to the surface 520. Each of the holes 532 are spaced from an upper edge 534 of the body 504, such that each of the holes 532 extending through the second or curved portion 508 as well as the first or base portion 506. As described above, the holes 532 correspond to a location on the surface 520 for application of adhesive 522, such that the holes 532 increase airflow to the adhesive 522 to quickly cure the adhesive 522. In an embodiment, one of the holes 532 is aligned with the second protrusion 526. As shown in FIG. 17, the first and second protrusions 510, 526 are aligned centrally with respect to the body 504, with the width 512 of the first protrusion 510 being greater than a width 534 of the second protrusion 526 between outer edges 536 of the second protrusion 526.

FIGS. 21-24 illustrate a system 600 according to one or more embodiments of the present disclosure. The system 600 includes a brace 602 and an anchor 604. Although FIGS. 21-24 illustrate a single brace 602 and anchor 604 pair, it is to be appreciated that embodiments of the present disclosure include two anchor brace pairs that are configured to be coupled to opposite sides of a toe nail of a user, as described herein. As such, the second anchor brace pair can have the same or similar features to the anchor brace pair described with reference to FIGS. 21-24.

The brace 602 is structured to be coupled to the anchor 604 in a use configuration and is further structured to be removed and separated from the anchor 604 when not in use. As such, the brace 602 is removably coupled to the anchor 604. As with the other systems described herein, the system 600 is structured to be coupled to a toenail of a user, in one or more embodiments. Specifically, the anchor 604 includes a base 606 and a flange 608 extending from the base 606, wherein a bottom surface of the base 606 and the flange 608 receive adhesive to couple the anchor to the toenail. The anchor 604 further includes a plurality of protrusions 610 extending from the base 606. The anchor 604 includes three protrusions 610 spaced equidistant between sides of the anchor 604, in one or more embodiments. In some embodiments, the anchor 604 includes more or less than three protrusions 610. Each of the protrusions 610 includes a hole 612 extending through the protrusion 610 from a top surface of the anchor 604 to the bottom surface of the anchor 604, as more clearly shown in FIG. 23.

The brace 602 includes a support 614 and extensions or protrusions 616 extending from the support 614. Each of the extensions 616 has a size and a shape to be received in a corresponding one of the holes 612 in the protrusions 610 of the anchor 604. In one or more embodiments, the extensions 616 are coupled to the protrusions 610 with a friction fit relative to the holes 612. As such, the extensions 616 may have a width or thickness, or both, that is greater a width or thickness of the holes 612. In other embodiments, there is a small clearance between outer edges or surfaces of the extensions 616 and the sidewall surfaces of the protrusions 610 around the holes 612, such that the coupling between the extensions 616 and the protrusions 610 is a clearance fit.

The support plate 614 extends beyond an outer edge or surface of each of the extensions 616 proximate the plate 614. Further, a length of each of the extensions 616 is greater than a height or length of each of the protrusions 610 and the holes 612, such that when the brace 602 is coupled to the anchor 604, the support plate 614 is spaced from the top surface of the protrusions by a gap or space 618. As such, the support plate 614 forms a lip such that when the brace 602 is coupled to the anchor 604 (e.g., the extensions 616 are received in the holes 612 of the protrusions 610), a user can attach a rubber band or other elastic member to each of the anchor brace pairs in the space 618 between the support plate 614 and the protrusions 610. A size of the space 618 can be selected changing the length of the extensions 616 relative to the length or height of the protrusions 610. The space 618 is at least as wide as various elastic members selected for use with the system 600, in one or more embodiments. The elastic member is held in place by the lip (e.g., the portion extending beyond the extensions 616) of the support plate 614 and applies a force to the brace 602 via the protrusions 610 that tends to pull opposing braces 602 towards each other. This force is distributed to the anchor 604 and the flange 608 attached to the nail and results in a generally upward force on the nail, as described herein. In some embodiments, the length of the extensions 16 may be the same as the height or length of the protrusions 610 such that the space 618 is omitted. The support plate 614 may then include a channel or groove for receiving the elastic member, or a protrusion for securing the elastic member, as described herein.

Figure 21:
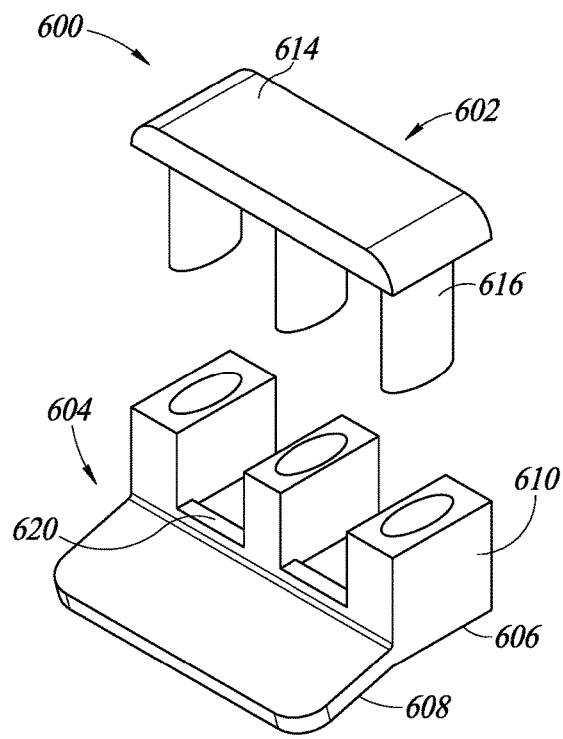
FIGS. 21-24 are views of one or more embodiments of a system for correcting an ingrown nail according to the present disclosure including an anchor with holes through protrusions of the anchor and a brace with extensions structured to be received in the holes.
Figure 22:
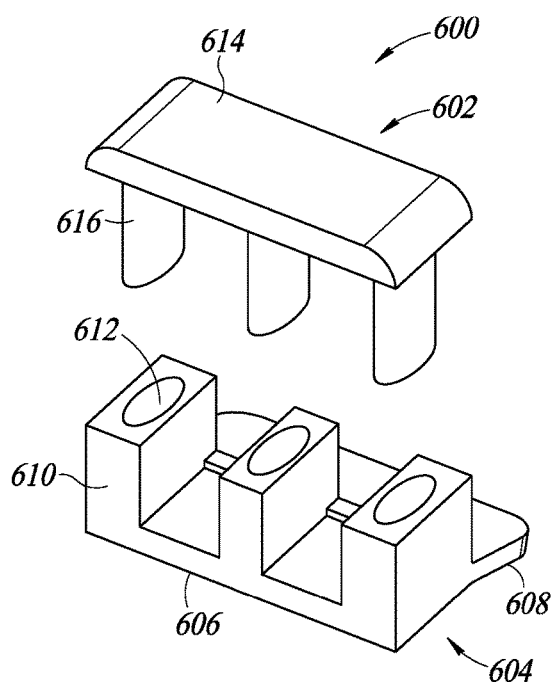

The system 600 further includes ridges 620 coupled to consecutive ones of the plurality of protrusions 610. The ridges 620 are coupled to consecutive ones of the plurality of protrusions 610 to provide lateral support for the protrusions 610. In one or more embodiments, the ridges 610 may be omitted. Further, FIG. 22 shows that the flange 608 of the anchor 604 may be at an angle relative to the base 606. In other words, in one or more embodiments, the base 606 of the anchor 604 is flat and planar and lies in a horizontal plane. The flange 608 extends at an angle between 0 and 180 degrees relative to the base 606. As shown in FIG. 21 and FIG. 22, the flange 608 extends below a plane containing the base 606, which helps adapt the anchor 604 to the shape of a typical toenail, while also distributing the force applied by the elastic member and the brace 602 to the flange 608 so that the flange 608 can apply tension to an ingrown toe nail, as described herein. The design and orientation of the flange 608 concentrates tension toward an outer portion of the flange 608, such that maximum force is applied to the ingrown nail at the edges of the nail.

Figure 23:
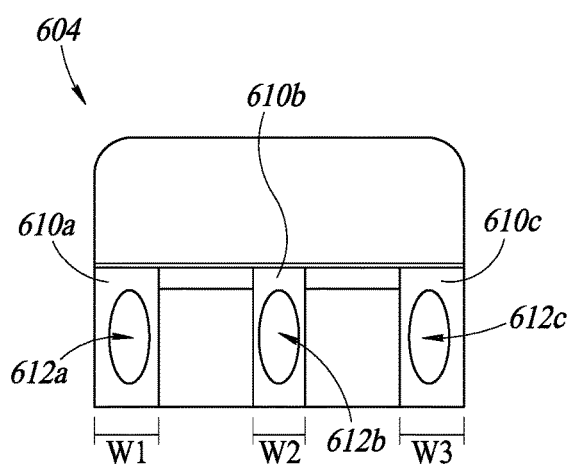
Figure 24:
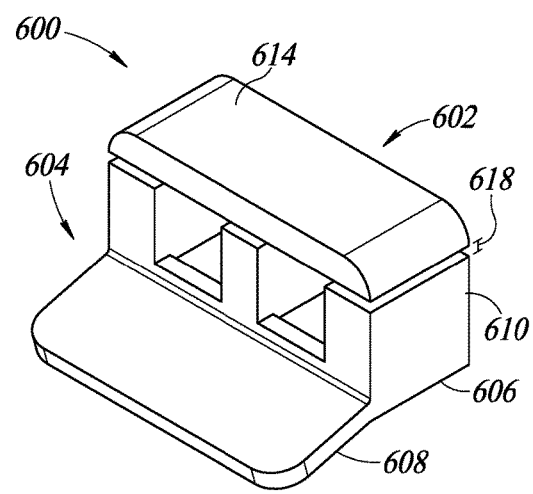

FIG. 23 illustrates that the plurality of protrusions 610 includes first, second, and third protrusions 610a, 610b, 610c, respectively, each having a width. Specifically, the first protrusion 610a has a first width W1, the second protrusion 610b has a second width W2 and the third protrusion 610c has a third width W3. In one or more embodiments, the first and third widths W1, W3 are equal and greater than the second width W2. In other embodiments, all of the widths W1, W2, W3 are equal, while in yet further embodiments, the second width W2 is greater than the first and third widths W1, W3. The first and third widths W1, W3 may be greater than the second width W2 because the stress applied to the system 600 at outer regions of the anchor 604 (e.g., regions corresponding to the first and third protrusions 610a, 610c) may be greater than the stress applied towards a center of the system 600. As such, the thicker outer protrusions 610a, 610c have a greater width or thickness to counteract that stress and improve reliability of the anchor 604. Further, each of the protrusions 610a, 610b, 610c includes a respective hole 612a, 612b, 612c.

As shown in FIG. 23, the first hole 612a and the third hole 612c are offset relative to a center of the first and third protrusions 610a, 610c. In other words, the first hole 612a and the third hole 612c are disposed closer to a surface of each of the first and third protrusions 610a, 610c facing the second protrusion 610b than a surface of each of the first and third protrusions 610a, 610c facing away from the second protrusion 610b. The hole 612b is centered with respect to the second protrusion 610b, in one or more embodiments. In further embodiments, each of the holes 612a, 612b, 612c, are centered with respect to corresponding ones of the protrusions 610a, 610b, 610c.

When a user applies the system 600, the user begins by cleaning a surface of the nail to which the system 600 is to be coupled. Then, the user applies adhesive to the bottom surface of the base 606 and the flange 608 of each anchor 604. The user then couples each anchor 604 to the toe nail at opposite edges (e.g. left and right sides) of the nail. One of the anchors 604 is attached to the edge of the nail that is ingrown, or both anchors 604 may be attached to the edge of the nail that is ingrown if both edges of the nail are ingrown. The holes 612 through the protrusions 610 of each anchor 604 allow the adhesive, which may be glue for example, to cure proximate a center of the bottom surface of each anchor 604. If the anchors 604 are not secured to the nail after the first or subsequent attempts, the above steps can be repeated until the anchors 604 are securely attached to the nail.

Then, the user aligns each brace 602 with a corresponding anchor 604 and inserts the extensions 616 of the braces 602 into the holes 612 in the protrusions 610 of the anchors 604. Once the braces 602 are secure, the user selects an elastic member according to the desired tension to be applied (e.g., different size rubber bands with different elastic properties, in one or more embodiments), and couples the elastic member to the system 600 by securing the elastic member in the space 618 between the braces 602 and the anchors 604. The elastic member provides a force on the braces 602 towards a center of the nail through the protrusions 610. The force is distributed to the flanges 608 of the anchors 604 secured to edges of the nail. The flanges 608 and the anchors 604 act as a fulcrum to pull on the nail in a generally upward direction, such that the ingrown nail is raised back to the nail bed over time.

When the system 600 is not selected to be in use, but treatment is ongoing, the user may remove the elastic member and then remove the braces 602 from the anchors 604. The anchors 604 have a low profile such that the user can wear socks and shoes, or participate in other activities, without impairment. When the user desires to resume treatment, the user simply reconnects the braces 602 to the anchors 604 and reattaches the elastic member. Over time, the user can select different elastic members depending on the treatment status (e.g., at the initial stages of treatment, an elastic member exerting more force on the braces 602 may be selected compared to the later stages of treatment where an elastic member with less force may be selected) or on the desired amount of time until the nail is cured. As such, a user can select their treatment schedule according to times that are convenient. Meanwhile, the system 600 does not impede the user from carrying out normal daily activities. Once treatment is finished, the user can remove the anchors 604 from the nail and any remaining adhesive using a solvent, in one or more embodiments.

As such, the systems, devices, and methods described herein provide continuous tension on the ingrown nail of user to correct the nail in less time than other known systems. Moreover, because the systems, devices, and methods generate a generally upward force on the nail, there is little to no pain for the user from treatment and in fact, pain from the ingrown nail is typically reduced for the user during treatment. The anchors and braces, or other devices, described herein are small enough that they do not significantly impact the day to day activities of the user. Moreover, the braces can be removed in some embodiments to further prevent disruption to the day to day activities of the user during treatment. Because the amount of tension on the nail can be varied, the systems, devices, and methods described herein can be used with all different severities of ingrown nails, including in severe cases, to correct the ingrown nail.

In the above description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with devices and systems for correcting ingrown toenails have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to." Further, the terms "first," "second," and similar indicators of sequence are to be construed as interchangeable unless the context clearly dictates otherwise.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" or other like phrases, such as "in one or more embodiments" or "in some embodiments" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its broadest sense that is as meaning "and/or" unless the content clearly dictates otherwise.

The relative terms "approximately" and "substantially," when used to describe a value, amount, quantity, or dimension, generally refer to a value, amount, quantity, or dimension that is within plus or minus 5% of the stated value, amount, quantity, or dimension, unless the context clearly dictates otherwise. It is to be further understood that any specific dimensions of components or features provided herein are for illustrative purposes only with reference to the various embodiments described herein, and as such, it is expressly contemplated in the present disclosure to include dimensions that are more or less than the dimensions stated, unless the context clearly dictates otherwise.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system, comprising:
a first anchor having a flat and planar base and a plurality of protrusions extending from the base with a hole extending through each of the plurality of protrusions of the first anchor, the plurality of protrusions of the first anchor spaced from each other in a length direction of the base of the first anchor with each protrusion of the plurality of protrusions of the first anchor extending across an entire width of the base of the first anchor, the first anchor further including a flange coupled to the base of the first anchor and extending below a plane containing the base of the first anchor, the flange of the first anchor extending away from a peripheral edge of the base of the first anchor with the plurality of protrusions of the first anchor terminating at the peripheral edge of the base of the first anchor;
a second anchor having a flat and planar base and a plurality of protrusions extending from the base with a hole through each of the plurality of protrusions of the second anchor, the plurality of protrusions of the second anchor spaced from each other in a length direction of the base of the second anchor with each protrusion of the plurality of protrusions of the second anchor extending across an entire width of the base of the second anchor, the second anchor further including a flange coupled to the base of the second anchor and extending below a plane containing the base of the second anchor, the flange of the second anchor extending away from a peripheral edge of the base of the second anchor with the plurality of protrusions of the second anchor terminating at the peripheral edge of the base of the second anchor;
a first brace having a support plate and a plurality of extensions coupled to the support plate of the first brace, each of the plurality of extensions of the first brace structured to be removably positioned within a corresponding hole in the plurality of protrusions of the first anchor to removably couple the first brace to the first anchor, the first brace being separate and distinct from the first anchor;

a second brace having a support plate and a plurality of extensions coupled to the support plate of the second brace, each of the plurality of extensions of the second brace configured to be removably positioned within a corresponding hole in the plurality of protrusions of the second anchor to removably couple the second brace to the second anchor, the second brace being separate and distinct from the second anchor; and a resilient connection member structured to be removably coupled to the first brace and the second brace, wherein the first anchor and the second anchor are structured to be coupled to a toenail of a user with the flange of the first anchor and the flange of the second anchor positioned further from a center of the toenail than the base of the first anchor and the base of the second anchor, respectively, and where the flange of the first anchor and the flange of the second anchor is configured to be positioned facing an outer surface of the toenail of the user, and wherein the resilient connection member is structured to act with a force to draw the first anchor and the second anchor towards each other to apply a tensile force to the toenail of the user.

2. The system of claim 1, wherein the plurality of protrusions of the first anchor include exactly three protrusions that are spaced equidistant from each other across the base of the first anchor.

3. The system of claim 1, wherein the plurality of protrusions of the second anchor include exactly three protrusions that are spaced equidistant from each other across the base of the second anchor.

4. The system of claim 1, wherein a first one of the plurality of protrusions of the first anchor has a first width and a second one of the plurality of protrusions of the first anchor has a second width less than the first width.

5. The system of claim 4 wherein a third one of the plurality of protrusions of the first anchor has a third width equal to the first width and greater than the second width.

6. The system of claim 1 wherein the flange of the first anchor is at an angle to the base of the first anchor between and excluding 0 degrees and 90 degrees.

7. The system of claim wherein the hole extending through a first protrusion of the plurality of protrusions of the first anchor is offset with respect to a center of a top surface of the first protrusion of the first anchor and the hole extending through a second protrusion of the plurality of protrusions of the second anchor is centered with respect to a top surface of the second protrusion of the second anchor.

8. The system of claim 1, wherein the plurality of protrusions of the first anchor include a first protrusion and a second protrusion positioned at opposite outer sides of the base of the first anchor and a third protrusion centered with respect to the first protrusion and the second protrusion.

9. The system of claim 1 wherein the flange of the second anchor is at an angle to the base of the second anchor between 15 degrees and 75 degrees.

10. The system of claim 1, wherein the plurality of extensions of the first brace have a height that is greater than a height of the plurality of protrusions of the first anchor to define a first space between a top surface of the plurality of protrusions of the first anchor and the support plate of the first brace, and wherein the plurality of extensions of the second brace have a height that is greater than a height of the plurality of protrusions of the second anchor to define a second space between a top surface of the plurality of protrusions of the second anchor and the support plate of the second brace, the resilient connection member structured to be received in the first space and the second space in contact with the plurality of extensions of the first brace and the plurality of extensions of the second brace with movement of the resilient connection member restricted in a first direction via the support plate of the first brace and the support plate of the second brace, and movement of the resilient connection member restricted in a second direction opposite to the first direction via the top surface of the plurality of protrusions the first anchor and the top surface of the plurality of protrusions of the second anchor.

11. A method comprising:

connecting a first anchor to a first location on a toenail, including coupling both a flat and planar base of the first anchor and a flange of the first anchor extending from the base of the first anchor to an outer surface of the toenail with the flange of the first anchor extending from an outer peripheral edge of the base of the first anchor to a location below a plane containing the flat and planar base of the first anchor, and further including arranging the flange of the first anchor further from a center of the toenail than the base of the first anchor;

connecting a second anchor to a second location on the toenail, including coupling both a flat and planar base of the second anchor and a flange of the second anchor extending from the base of the second anchor to the outer surface of the toenail with the flange of the second anchor extending from an outer peripheral edge of the base of the second anchor to a location below a plane containing the flat and planar base of the second anchor, and further including arranging the flange of the second anchor further from a center of the toenail than the base of the second anchor;

coupling a first brace to the first anchor, the coupling including positioning a plurality of extensions of the first brace in corresponding holes through a plurality of protrusions of the first anchor with the plurality of protrusions spaced across the base of the first anchor and terminating at an interface between the base of the first anchor and the flange of the first anchor, and defining a first space between a support plate of the first brace coupled to the plurality of extensions of the first brace and a top surface of the plurality of protrusions of the first anchor;

coupling a second brace to the second anchor, the coupling including positioning a plurality of extensions of the second brace in corresponding holes through a plurality of protrusions of the second anchor with the plurality of protrusions spaced across the base of the second anchor and terminating at an interface between the base of the second anchor and the flange of the second anchor, and defining a second space between a support plate of the second brace that is coupled to the plurality of extensions of the second brace and a top surface of the plurality of protrusions of the second anchor; and attaching a first resilient connection member that extends from the first brace to the second brace, the attaching including positioning the first resilient connect member in the first space and the second space with the first resilient connection member exerting a first force on the plurality of extensions of the first brace and the plurality of extensions of the second brace, and restricting movement of the first resilient connection member with the support plate of the first brace, the support plate of the second brace, the top surface of the plurality of protrusions of the first anchor, and the top surface of the plurality of protrusions of the second anchor to draw the first anchor towards the second anchor at a first point in time.

12. The method of claim 11 further comprising:
removing the first resilient connection member from the first and second brace at a second point in time.

13. The method of claim 12 further comprising, after the removing the first resilient connection member at the second point in time:
attaching a second resilient connection member that extends from the first brace to the second brace at the second point in time, the attaching the second resilient connection member including the second resilient connection member exerting a second force different from the first force to draw the first anchor towards the second anchor.

14. The method of claim 11 further comprising:
removing the first resilient connection member from the first and second braces at a second point in time; and
removing the first and second brace from the first and second anchors, respectively, at the second point in time.

15. The method of claim 14 further comprising, after the removing the first and second brace at the second point in time:
re-attaching the first and second brace to the first and second anchors, respectively, at a third point in time different than the second point in time; and
re-attaching the first resilient connection member to the first and second braces at the third point in time.

16. A system, comprising:
a first anchor configured to be coupleable to a first location on an outer surface of a toenail of a user, including:
   a base having a top surface and a bottom surface opposite and parallel to the top surface, the base including a sidewall extending between the top surface and the bottom surface:
   a plurality of protrusions extending vertically from the top surface of the base of the first anchor and spaced from each other in a length direction of the base of the first anchor, each of the plurality of protrusions of the first anchor extending horizontally across the top surface in a width direction of the base of the first anchor from a first outer peripheral edge to a second outer peripheral edge of the base of the first anchor opposite the first outer peripheral edge of the base of the first anchor;
   a plurality of holes, each of the plurality of holes of the first anchor extending through a respective one of the plurality of protrusions of the first anchor and through an entirety of the base of the first anchor from the top surface to the bottom surface of the base of the first anchor; and
   a flange extending from an entirety of the sidewall associated with the first outer peripheral edge of the base of the first anchor and terminating below a plane containing the bottom surface of the base of the first anchor;
a second anchor configured to be coupleable to a second location on the outer surface of the toenail of the user opposite the first location, including:
   a base having a top surface and a bottom surface opposite and parallel to the top surface, the base including a sidewall extending between the top surface and the bottom surface;
   a plurality of protrusions extending vertically from the top surface of the base of the second anchor and spaced from each other in a length direction of the base of the second anchor, each of the plurality of protrusions of the second anchor extending horizontally across the top surface in a width direction of the base of the second anchor from a first outer peripheral edge to a second outer peripheral edge of the base of the second anchor opposite the first outer peripheral edge of the base of the second anchor;
   a plurality of holes, each of the plurality of holes extending through a respective one of the plurality of protrusions of the second anchor and through an entirety of the base of the second anchor from the top surface to the bottom surface of the base of the second anchor; and
   a flange extending from an entirety of the sidewall associated with the first outer peripheral edge of the base of the second anchor and terminating below a plane containing the bottom surface of the base of the second anchor;
a first brace having a support plate and a plurality of extensions coupled to the support plate, each of the plurality of extensions extending vertically downward from the support plate of the first brace and structured to be removably positioned within a corresponding hole of the plurality of holes of the first anchor to removably couple the first brace to the first anchor, the support plate of the first brace extending beyond boundaries of each of the plurality of extensions of the first brace to define a first lip;
a first space between a top surface of the plurality of protrusions of the first anchor and the support plate of the first brace;
a second brace having a support plate and a plurality of extensions coupled to the support plate, each of the plurality of extensions extending vertically downward from the support plate of the second brace and structured to be removably positioned within a corresponding hole of the plurality of holes of the second anchor to couple the second brace to the second anchor, the support plate of the second brace extending beyond boundaries of each of the plurality of extensions to define a second lip;
a second space between a top surface of the plurality of protrusions of the second anchor and the support plate of the second brace; and
a resilient connection member structured to be removably coupled to the first brace and the second brace, the resilient connect member structured to be received in the first space and the second space in direct contact with the plurality of extensions of the first brace and the plurality of extensions of the second brace and secured in the first space and the second space via the first lip, the second lip, the top surface of the plurality of protrusions of the first anchor, and the top surface of the plurality of protrusions of the second anchor, the resilient connection member further structured to act with a force to draw the first anchor and the second anchor towards each other to apply a tensile force to opposite sides of the outer surface of the toenail of the user.

17. The system of claim 16, wherein the plurality of extensions of the first brace include exactly three extensions spaced equidistant from each other relative to the support plate of the first brace.

18. The system of claim 16, wherein the plurality of protrusions of the first anchor includes exactly three protrusions with a first protrusion and a second protrusion aligned with end faces of opposite sides of the first anchor and a third protrusion centered with respect to the first protrusion and the second protrusion.

19. The system of claim 16 wherein the first space corresponds to a difference between a height of the plurality extensions of the first brace and a height of the plurality of protrusions of the first anchor.

20. The system of claim 16, wherein outer surfaces of the plurality of protrusions of the first anchor are aligned and planar with outer surfaces of the support plate of the first brace in response to the plurality of extensions of the first brace being received in the plurality of holes in the plurality of protrusions of the first anchor to couple the first brace to the first anchor.

\* \* \* \* \*

UNITED STATES PATENT AND TRADEMARK OFFICE
CERTIFICATE OF CORRECTION

PATENT NO. : 11,672,689 B2
APPLICATION NO. : 16/681585
DATED : June 13, 2023
INVENTOR(S) : Jordan Schweitzer Page 1 of 1

It is certified that error appears in the above-identified patent and that said Letters Patent is hereby corrected as shown below:

In the Claims

Column 19, Claim 7, Line 45:
"The system of claim wherein" should read: --The system of claim 1, wherein--.

Signed and Sealed this
Twenty-fifth Day of February, 2025

Coke Morgan Stewart
*Acting Director of the United States Patent and Trademark Office*